United States Patent
Yamashita et al.

(10) Patent No.: US 9,657,039 B2
(45) Date of Patent: May 23, 2017

(54) PRODUCTION METHOD FOR ALKOXYSILANES

(71) Applicant: NATIONAL INSTITUTE OF ADVANCED INDUSTRIAL SCIENCE AND TECHNOLOGY, Tokyo (JP)

(72) Inventors: Hiroshi Yamashita, Ibaraki (JP); Makiko Hatori, Ibaraki (JP); Michiyo Yoshinaga, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 14/772,741

(22) PCT Filed: Mar. 5, 2014

(86) PCT No.: PCT/JP2014/055584
§ 371 (c)(1),
(2) Date: Sep. 3, 2015

(87) PCT Pub. No.: WO2014/136822
PCT Pub. Date: Sep. 12, 2014

(65) Prior Publication Data
US 2016/0002271 A1 Jan. 7, 2016

(30) Foreign Application Priority Data
Mar. 7, 2013 (JP) .................. 2013-045262

(51) Int. Cl.
*C07F 7/02* (2006.01)
*C07F 7/18* (2006.01)
*B01J 29/08* (2006.01)
*B01J 29/18* (2006.01)
*B01J 29/40* (2006.01)
*C07F 7/08* (2006.01)
*B01J 29/70* (2006.01)
*B01J 31/10* (2006.01)

(52) U.S. Cl.
CPC ............ *C07F 7/1892* (2013.01); *B01J 29/08* (2013.01); *B01J 29/18* (2013.01); *B01J 29/40* (2013.01); *B01J 29/7007* (2013.01); *B01J 31/10* (2013.01); *C07F 7/0834* (2013.01); *C07F 7/1804* (2013.01); *C07F 7/184* (2013.01); *C07F 7/1836* (2013.01); *B01J 2229/12* (2013.01); *B01J 2229/32* (2013.01); *C07F 7/02* (2013.01)

(58) Field of Classification Search
CPC ....................................................... C07F 7/02
USPC ........................................ 556/469, 470, 483
See application file for complete search history.

(56) References Cited

U.S. PATENT DOCUMENTS

| | | | |
|---|---|---|---|
| 6,005,132 A | 12/1999 | Weidner et al. | |
| 2009/0149554 A1 | 6/2009 | Ishikawa et al. | |

FOREIGN PATENT DOCUMENTS

| | | | |
|---|---|---|---|
| JP | 1-117890 A | 5/1989 | |
| JP | 4-295486 A | 10/1992 | |
| JP | 5-255348 A | 10/1993 | |
| JP | 5-255349 A | 10/1993 | |
| JP | 2000-500779 A | 1/2000 | |
| JP | 2004-269465 A | 9/2004 | |
| JP | 2005-008563 A | 1/2005 | |
| JP | 2007-070353 A | 3/2007 | |

OTHER PUBLICATIONS

International Search Report for International Application No. PCT/JP2014/055584, mailed on Apr. 15, 2014, in 2 pages.
International Preliminary Report on Patentability and Written Opinion of the International Searching Authority for International Application No. PCT/JP2014/055584, mailed on Sep. 17, 2015, in 8 pages.
Hasegawa et al., "Transesterification Reaction of Tetraethoxysilane and Butyl Alcohols," *Bull. Chem. Soc. Jpn.*, vol. 61, pp. 4087-4092 (1988).
Helferich et al., "The transesterification of Orthosilicate esters," *Chem. Ber.*, vol. 80, pp. 163-164 (1947).
Ito et al., "Alcoholysis Equilibria of Triethylalkoxysilanes Catalyzed by Iodine or Iodine Monobromide," *Bull. Chem. Soc. Jpn.*, vol. 55, pp. 2973-2975 (1982).
Larsson, "About some of the reaction products of dimethyldiethoxysilane with aminoalcohols," *Acta Cemica Scandinavica*, vol. 8(6), pp. 898-900 (1954).
Mehrotra et al., "(Aminoalkoxy)Silanes; II. Synthesis of Vinyl-and Phenyl (Aminoalkoxy) Silanes," *Journal of Organometallic Chemistry*, vol. 25, pp. 359-365 (1970).
Voronkov et al., "Alkoxysilanes; XXII. Alcoholysis of Ethoxytrimethylsilane," *J. Gen. Chem.*, USSR, vol. 37, pp. 2630-2631 (1967).

*Primary Examiner* — Elvis O Price
(74) *Attorney, Agent, or Firm* — Knobbe, Martens, Olson & Bear LLP

(57) ABSTRACT

Provided is a method for efficiently producing alkoxysilanes that are useful as various functional chemicals. In order to produce alkoxysilanes efficiently, an ethoxy- or methoxysilane and an alcohol are caused to react using, as a catalyst, for instance an inorganic solid acid having a regular-pore and/or layered structure. Zeolites, montmorillonites or the like can be used as the inorganic solid acid. When a zeolite is used as the catalyst, the silica/alumina ratio of the zeolite ranges preferably from 5 to 1000. The reaction can be promoted through irradiation of microwaves.

8 Claims, No Drawings

PRODUCTION METHOD FOR ALKOXYSILANES

CROSS-REFERENCE TO RELATED APPLICATIONS

This application is the U.S. National Phase under 35 U.S.C. §371 of International Application PCT/JP2014/055584, filed Mar. 5, 2014, which claims priority to JP Application No. 2013-045262, filed Mar. 7, 2013.

TECHNICAL FIELD

The present invention relates to an efficient method for producing alkoxysilanes or the like.

BACKGROUND ART

Among alkoxysilanes, for instance trialkoxysilanes are used as silane coupling agents or the like for surface modification of inorganic materials, while tetraalkoxysilanes are widely used as starting materials of silica, zeolites, ceramics and organic/inorganic hybrid materials, according to sol-gel methods. Silanes substituted with organic groups or hydrogen atoms are functional chemicals that are used as reagents for precise synthesis, and as synthesis intermediates, in pharmaceuticals, agrichemicals, electronic materials and the like.

Ethoxy groups or methoxy groups are often used as the alkoxy groups in alkoxysilanes, but in recent years attention has been devoted to alkoxysilanes in which some or all the ethoxy groups or methoxy groups are substituted by other alkoxy groups, for the purpose of controlling the reactivity of the alkoxysilanes, or imparting functionality to the latter.

Catalysts such as acids and bases have been conventionally used to conduct reactions in which silanes having ethoxy groups or the like are caused to react with alcohols, to substitute the ethoxy groups or the like by alkoxy groups. Acid or base catalysts that have been used thus far include, for instance, trichloroacetic acid, piperidine or the like (Non-Patent Literature 1). Examples have also been reported in which halogen compounds, such as iodine or iodine bromide, are used as catalysts (Non-Patent Literature 2). Other instances have been reported where metallic sodium is used in reactions of tetramethoxysilane and di- or triethoxysilane (Non-Patent Literature 3 to 5). Also, examples are known where reactions of tetramethoxysilane, methyltrimethoxysilane and the like are conducted using organic or inorganic solid catalysts (Non-Patent Literature 6, Patent Literature 1 to 4).

However, these methods have the following problems: (1) when the catalyst is a liquid-state catalyst or is soluble in a solution, for instance as in the case of trichloroacetic acid or piperidine, separation and recovery of the catalyst after the reaction is not easy; (2) when the catalyst comprises iodine, the latter is not easy to handle easily due to the corrosive character of iodine; (3) when sodium is the catalyst, the latter is not easy to handle safely, since sodium is sensitive to moisture or the like; (4) it is ordinarily difficult to selectively make just some ethoxy groups or methoxy groups, in a plurality thereof, into other alkoxy groups; and (5) in the case of solid catalysts, the reaction system is a heterogeneous system, and, accordingly, reactions are slow and require a long reaction time, depending on the type of starting materials and reaction conditions. A demand arose thus for more industrially advantageous methods.

Among conventional methods, those that rely on inorganic solid catalysts are found to be superior to methods relying on organic solid catalyst as regards for instance the thermal stability and durability of the catalyst. However, specific usage examples known in the art, in the production reactions that utilize specific starting materials, include just calcium oxide, silica-alumina N-633HN (by Nikki Chemical Co., Ltd.), niobic acid, activated clay, protonated Y zeolites and thallium oxide (Examples 2, 4, 5 and 6 in Patent Literature 2, Examples 4 and 5 in Patent Literature 3). These examples are problematic in that the starting silane is used in excess with respect to the alcohol, and the yield of the generated silanes (total of mono-, di- and/or trisubstituted silane) with respect to the starting silane is often low (yields of about 10%, about 12%, about 12% and about 10%, respectively, in Examples 2, 4, 5 and 6 of Patent Literature 2, and yield of about 16% in Example 5 of Patent Literature 3), or are problematic in that the selectivity for the monosubstituted product, in which only some methoxy groups of the starting material are substituted by alkoxy groups, is not high (ratios of the mono-, di- and trisubstituted products of 57.3:35.6:7.1 in Example 4 of Patent Literature 3). More effective inorganic solid catalysts were thus desirable. Although there is no detailed explanation concerning how to obtain protonated Y-type zeolites, used as described above, it is deemed that the silica/alumina ratio ($SiO_2/Al_2O_3$ ratio) is 136/(56×0.5)=4.86, in the light of the disclosure "Bronsted acid sites ($H^+$) were generated through substitution of Na ions by $NH_4^+$, on the surface of Y-type zeolite ($Na_{56}(AlO_2)_{56}(SiO_2)_{136} \cdot nH_2O$) particles, and desorption of $NH_3$ through a heating treatment at 300° C." (Patent Literature 3, paragraph [0038], table 2, footnote 2). Nothing, however, is disclosed regarding Y-type zeolites having other silica/alumina ratios, or regarding zeolites of structures other than Y type, while the effectiveness of the foregoing zeolites is likewise unknown.

Non-Patent Literature 1: J. Gen. Chem. USSR, 37, 2630-2631 (1967)
Non-Patent Literature 2: Bull. Chem. Soc. Jpn., 55, 2973-2975 (1982)
Non-Patent Literature 3: Chem. Ber., 80, 163-164 (1947)
Non-Patent Literature 4: Acta Chem. Scand., 8, 898-900 (1954)
Non-Patent Literature 5: J. Organomet. Chem., 25, 359-365 (1970)
Non-Patent Literature 6: Bull. Chem. Soc. Jpn., 61, 4087-4092 (1988)
Patent Literature 1: Japanese Patent Application Publication No. H4-295486
Patent Literature 2: Japanese Patent Application Publication No. H5-255348
Patent Literature 3: Japanese Patent Application Publication No. H5-255349
Patent Literature 4: Japanese Patent Application Publication No. 2004-269465

DISCLOSURE OF THE INVENTION

In the light of the above considerations, it is an object of the present invention to produce more efficiently alkoxysilanes in which ethoxy groups or methoxy groups in a starting alkoxysilane are converted other alkoxy groups.

As a result of diligent research directed at attaining the above goal, the inventors arrived at the following findings, among others: (1) reactions between an alcohol and an ethoxy group- or methoxy group-containing alkoxysilane proceed smoothly in the presence of a solid acid catalyst such as zeolites, montmorillonites or the like having a regular-pore/layered structure, and alkoxysilanes are obtained with good efficiency; (2) zeolite catalysts of USY type, beta type, Y type and the like are effective, and zeolite catalysts having a silica/alumina ratio in the range 5 to 1000 are particularly effective; (3) By conducting the reaction using a specific inorganic solid acid catalyst and by controlling temperature, time and so forth, it becomes possible to convert selectively just some ethoxy groups or methoxy groups, in a plurality thereof, to other alkoxy groups, and to produce silanes having tertiary alkoxy groups, through reaction with tertiary alcohols; and (4) the reaction is promoted when irradiating microwaves into a reaction system, of an alkoxysilane and an alcohol, in which a solid acid catalyst is used; and perfected the present invention on the basis of the above findings.

The production method of the present invention has the following characterizing features.

(1) The catalyst is easy to procure, easy to handle, and is moreover highly safe.

(2) Separation, recovery and so forth of the catalyst are easy, since the catalyst is a solid and the reaction is a heterogeneous system.

(3) By controlling the reaction conditions, such as the type of catalyst, it becomes possible to convert, substantially selectively, just some ethoxy groups or methoxy groups, in a plurality thereof, to other alkoxy groups, and to produce silanes having tertiary alkoxy groups.

(4) The reaction can be promoted through irradiation of microwaves.

The present production method allows lowering costs and increasing efficiency in production processes, and is accordingly found to be significantly more advantageous than conventional ones as regards, for instance, economy and environmental impact.

Specifically, the present application provides the following inventions.

(1) A method for producing alkoxysilanes, comprising a reaction step of reacting an alkoxysilane having an ethoxy group or a methoxy group, and an alcohol, in the presence of a catalyst, wherein
the alkoxysilane having an ethoxy group or methoxy group is an alkoxysilane represented by Formula (I);
the alcohol is an alcohol represented by Formula (II);
the catalyst is a solid acid catalyst; and
an alkoxysilane obtained in the reaction step is an alkoxysilane represented by Formula (III).

$$R^1_p R^2_q R^3_r Si(OR^4)_{4-(p+q+r)} \quad (I)$$

(In Formula (I), p, q, r and p+q+r are integers ranging from 0 to 3; $R^1$, $R^2$ and $R^3$ are each independently a hydrocarbon group having 1 to 23 carbon atoms, or a hydrogen atom; $R^4$ is independently an ethyl group or a methyl group; and in a case where $R^1$, $R^2$ and $R^3$ are hydrocarbon groups, some of the hydrogen atoms of the hydrocarbon groups may be substituted by groups that do not participate in the reaction);

$$ROH \quad (II)$$

(In Formula (II), R is a hydrocarbon group having 1 to 23 carbon atoms, and some of the hydrogen atoms in the hydrocarbon group may be substituted by groups that do not participate in the reaction);

$$R^1_p R^2_q R^3_r Si(OR^4)_{4-(p+q+r)-m}(OR)_m \quad (III)$$

(In Formula (III), the meanings of p, q and r, and $R^1$, $R^2$, $R^3$, $R^4$ and R are identical to those above; and m is an integer ranging from 1 to (4−(p+q+r))).

(2) The method for producing alkoxysilanes according to (1),
wherein the solid acid catalyst is an inorganic solid acid having a regular-pore and/or layered structure.

(3) The method for producing alkoxysilanes according to (2),
wherein the inorganic solid acid is a zeolite and/or a montmorillonite.

(4) The method for producing alkoxysilanes according to (3),
wherein the zeolite has a silica/alumina ratio (substance amount ratio) ranging from 5 to 1000.

(5) The method for producing alkoxysilanes according to (3),
wherein the zeolite is at least one zeolite type selected from the group consisting of USY type, beta type, Y type, mordenite type and ZSM-5 type.

(6) The method for producing alkoxysilanes according to any one of (3) to (5),
wherein an alkoxysilane, for which m in the Formula (III) is 1, is produced as a main product.

(7) The method for producing alkoxysilanes according to any one of (3) to (6),
wherein an alkoxysilane is produced in which R in the Formula (III) is a tertiary alkyl group.

(8) The method for producing alkoxysilanes according to any one of (1) to (7),
wherein the reaction step is performed under irradiation of microwaves.

By resorting to the production method of the present invention, an advantageous effect is elicited whereby it becomes possible to produce, more efficiently than in conventional methods, alkoxysilanes in which ethoxy groups or methoxy groups are substituted by alkoxy groups, aralkyloxy groups or alkenyloxy groups.

BEST MODE FOR CARRYING OUT THE INVENTION

The present invention will be explained next in detail.

The production method of the present invention is characterized by comprising a reaction step of reacting an alkoxysilane having an ethoxy group or a methoxy group with an alcohol, in the presence of a solid acid catalyst.

The alkoxysilane that is used as a starting material in the present invention is represented by Formula (I) below.

$$R^1_p R^2_q R^3_r Si(OR^4)_{4-(p+q+r)} \quad (I)$$

In Formula (I), p, q, r and p+q+r are integers ranging from 0 to 3. Further, $R^1$, $R^2$ and $R^3$ are each independently a hydrocarbon group having 1 to 23 carbon atoms, or a hydrogen atom, and $R^4$ is independently an ethyl group or a methyl group. In a case where $R^1$, $R^2$ and $R^3$ are hydrocarbon groups, some of the hydrogen atoms of the hydrocarbon groups may be substituted by groups that do not participate in the reaction.

Examples of hydrocarbon groups of $R^1$, $R^2$ and $R^3$ include, for instance, aryl groups, alkyl groups, aralkyl groups, alkenyl groups and alkynyl groups.

In a case where $R^1$, $R^2$ or $R^3$ is an aryl group, there can be used a monovalent aromatic organic group of a hydrocarbon ring system or a heterocyclic ring system. In a case of an organic group of a hydrocarbon ring system, the number of carbon atoms in the ring ranges preferably from 6 to 22, more preferably from 6 to 14. Specific examples of aromatic organic groups of a carbon ring system include, for instance, phenyl groups, naphthyl groups, anthryl groups, phenanthryl groups, pyrenyl groups, perylenyl groups and pentacenyl groups.

In a case where the aryl group is an organic group of a heterocyclic ring system, the heteroatom is sulfur, an oxygen atom or the like, and the number of carbon atoms in the ring ranges preferably from 4 to 12, more preferably from 4 to 8. Specific examples of aromatic organic groups of a heterocyclic ring system include, for instance, thienyl groups, benzothienyl groups, dibenzothienyl groups, furyl groups, benzofuryl groups and dibenzofuryl groups.

Preferably, p+q+r is equal to or smaller than 2.

Some of the hydrogen atoms in the above aryl groups may be substituted by groups that do not participate in the reaction. Specific examples of such groups include, for instance, alkyl groups having preferably 1 to 12, and more preferably 1 to 10 carbon atoms, alkoxy groups having preferably 1 to 12, and more preferably 1 to 10 carbon atoms, and halogen atoms. More specifically, examples of the groups include alkyl groups such as methyl groups, isopropyl groups, hexyl groups and octyl groups; alkoxy groups such as methoxy groups, ethoxy groups, isopropoxy groups, hexoxy groups and octoxy groups, and halogen atoms such as fluorine atoms, chlorine atoms and bromine atoms. Examples of other groups that do not participate in the reaction include, for instance, oxyethylene groups and oxyethyleneoxy groups being divalent groups, with bonding of the two carbon atoms in the ring.

Specific examples of aryl groups having these groups include, for instance, methylphenyl groups, ethylphenyl groups, hexylphenyl groups, methoxyphenyl groups, ethoxyphenyl groups, butoxyphenyl groups, octoxyphenyl groups, methyl(methoxy)phenyl groups, fluoro(methyl)phenyl groups, chloro(methoxy)phenyl groups, bromo(methoxy)phenyl groups, 2,3-dihydrobenzofuranyl groups, 1,4-benzodioxanyl groups and the like.

In a case where $R^1$, $R^2$ or $R^3$ is an alkyl group, the number of carbon atoms ranges preferably from 1 to 12, more preferably from 1 to 10, and some or all hydrogen atoms on carbons may be substituted by groups that do not participate in the reaction. Specific examples of groups that do not participate in the reaction include, for instance, alkoxy groups having 1 to 6 carbon atoms, alkoxycarbonyl groups having 1 to 6 carbon atoms, alkenyl carbonyloxy groups having 1 to 6 carbon atoms, dialkylamino group having 1 to 6 carbon atoms, cyano groups, oxiranyl groups, halogen atoms and the like. More specifically, instances of the alkoxy groups, alkoxycarbonyl groups, alkenyl carbonyloxy groups, dialkylamino groups and halogen atoms include, for example, alkoxy groups such as methoxy groups, ethoxy groups and hexoxy groups; alkoxycarbonyl groups such as methoxycarbonyl groups and propoxycarbonyl groups; alkenyl carbonyloxy groups such as isopropenyl carbonyloxy groups; dialkylamino groups such as dimethylamino groups and diethylamino groups; and halogen atoms such as fluorine atoms and chlorine atoms. Specific examples of the alkyl groups include, for instance, methyl groups, ethyl groups, propyl groups, butyl groups, sec-butyl groups, hexyl groups, cyclohexyl groups, octyl groups, decyl groups, 2-methoxyethyl groups, 3-ethoxypropyl groups, 2-methoxycarbonylethyl groups, 2-dimethylaminoethyl groups, 2-cyanoethyl groups, 3-chloropropyl groups and the like.

In a case where $R^1$, $R^2$ or $R^3$ is an aralkyl group, the number of carbon atoms ranges preferably from 7 to 23, more preferably from 7 to 16, and some or all hydrogen atoms on carbons may be substituted by groups that do not participate in the reaction. Specific examples of groups that do not participate in the reaction include, for instance, the groups mentioned in the case of the alkyl groups above. Specific examples of the aralkyl groups include, for instance, benzyl groups, phenethyl groups, 2-naphthylmethyl groups, 9-anthrylmethyl groups, (4-chlorophenyl)methyl groups, 1-(4-methoxyphenyl)ethyl groups and the like.

In a case where $R^1$, $R^2$ or $R^3$ is an alkenyl group or an alkynyl group, the number of carbon atoms ranges preferably from 2 to 23, more preferably from 2 to 20, and some or all hydrogen atoms on carbons may be substituted by groups that do not participate in the reaction. Specific examples of groups that do not participate in the reaction include, for instance, those exemplified in the case of the alkyl groups above, and also the aryl groups exemplified above. Specific examples of the alkenyl groups include, for instance, vinyl groups, 2-propenyl groups, 3-butenyl groups, 5-hexenyl groups, 9-decenyl groups, 2-phenylethenyl groups, 2-(methoxyphenyl)ethenyl groups, 2-naphthylethenyl groups, 2-anthrylethenyl groups, ethynyl groups, propargyl groups, 1-hexynyl groups, phenylethynyl group and the like.

Examples of combinations of $R^1$, $R^2$ and $R^3$ include, for instance, a combination of methyl groups and phenyl groups, a combination of methyl groups and vinyl groups, a combination of methyl groups and hydrogen atoms, a combination of methyl groups, phenyl groups and vinyl groups, and a combination of methyl groups, phenyl groups and hydrogen atoms.

Therefore, specific examples of alkoxysilanes having the $R^1$, $R^2$, $R^3$ groups include, for instance, trimethyl(methoxy)silane, trimethyl(ethoxy)silane, methylphenyldi(methoxy)silane, dimethyldi(methoxy)silane, dimethyldi(ethoxy)silane, methyltri(methoxy)silane, methyltri(ethoxy)silane, phenyltri(methoxy)silane, phenyltri(ethoxy)silane, vinyltri(methoxy)silane, vinyltri(ethoxy)silane, ethynyltri(ethoxy)silane, (phenylethynyl)tri(methoxy)silane, tri(methoxy)silane, tri(ethoxy)silane, tetra(methoxy)silane, tetra(ethoxy)silane and the like.

The alcohol that is caused to react with the above alkoxysilane is represented by Formula (II) below.

$$ROH \tag{II}$$

In Formula (II), R is a hydrocarbon group having 1 to 23 carbon atoms. Some of the hydrogen atoms in the hydrocarbon group may be substituted by groups that do not participate in the reaction.

Examples of the hydrocarbon group in R include, for instance, alkyl groups, aryl groups, aralkyl groups, alkenyl groups and alkynyl groups.

In a case where R is an alkyl group, the number of carbon atoms ranges preferably from 1 to 12, more preferably from 1 to 10, and some or all hydrogen atoms on carbons may be substituted by groups that do not participate in the reaction. Specific examples of groups that do not participate in the reaction include, for instance, those mentioned in the explanation of Formula (I) above for a case where $R^1$, $R^2$ or $R^3$ is an alkyl group. Specific examples of the alkyl groups include, for instance, methyl groups, ethyl groups, propyl groups, butyl groups, sec-butyl groups, tert-butyl groups, pentyl groups, amyl groups, tert-amyl groups, cyclohexyl groups, hexyl groups, octyl groups, decyl groups, 2-methoxyethyl groups, 3-ethoxy propyl groups, 2-methoxycarbonylethyl groups, 2-(isopropenyl carbonyloxy)ethyl groups, glycidyl groups, 2-dimethylaminoethyl groups, 2-cyanoethyl groups, 3-chloropropyl groups and the like.

In a case where R is an aryl group or an aralkyl group, the number of carbon atoms ranges preferably from 6 to 23, more preferably from 6 to 16, and some or all hydrogen atoms on carbons may be substituted by groups that do not participate in the reaction. Specific examples of groups that do not participate in the reaction include, for instance, the groups mentioned in the case of the alkyl groups above. Specific examples of these aryl groups and aralkyl groups include, for instance, phenyl groups, 4-methylphenyl groups, 2-naphthyl groups, benzyl groups, phenethyl groups, 2-naphthylmethyl groups, 9-anthrylmethyl groups, 4-chlorophenylmethyl groups, 1-(4-methoxyphenyl)ethyl groups and the like.

In a case where R is an alkenyl group or an alkynyl group, the number of carbon atoms ranges preferably from 2 to 23, more preferably from 2 to 20, and some or all hydrogen atoms on carbons may be substituted by groups that do not participate in the reaction. Specific examples of groups that do not participate in the reaction include, for instance, those mentioned in the case of the above alkyl group, and also those mentioned in the explanation of Formula (I) above for a case where $R^1$, $R^2$ or $R^3$ is an aryl group. Specific examples of these alkenyl groups and alkynyl groups include, for instance, 2-propenyl groups, 3-butenyl groups, 3-methyl-2-butenyl groups, 5-hexenyl groups, 9-decenyl groups, 3-phenyl-2-propenyl groups, 2-(methoxyphenyl)-2-propenyl groups, 3-naphthyl-2-propenyl groups, 3-anthryl-2-propenyl groups, propargyl groups, 2-butyn-1-yl groups, 3-phenyl-2-propyn-1-yl groups and the like.

Therefore, specific examples of the alcohol (II) having an alkyl group, an aryl group, an aralkyl group, an alkenyl group or an alkynyl group include, for instance, propanol, butanol, sec-butyl alcohol, tert-butyl alcohol, pentanol, 2-methyl-butanol, amyl alcohol, tert-amyl alcohol, hexanol, cyclohexanol, octanol, decanol, dodecanol, 3-methyl-2-butenol, 2-(dimethylamino)ethanol, 2-cyanoethanol, 3-chloropropanol, phenol, cresol, naphthol, benzyl alcohol, phenyl ethanol, naphthyl methanol, anthryl methanol, 3-methyl-2-butenol, 5-hexenol, 9-decenol, allyl alcohol, propargyl alcohol, (2-hydroxyethyl) methacrylate, glycidol and the like.

The molar ratio of the alcohol with respect to the starting alkoxysilane can be selected arbitrarily, but ranges ordinarily from 0.4 to 300, more preferably from 0.5 to 200, and yet more preferably from 0.5 to 150, in terms of the yield of the generated alkoxysilane with respect to the starting alkoxysilane.

In the present invention, an alkoxysilane represented by Formula (III) below is obtained through reaction of the alkoxysilane represented by Formula (I) above and the alcohol of Formula (II) above.

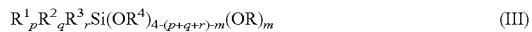

(In Formula (III), the meanings of p, q and r, and $R^1$, $R^2$, $R^3$, $R^4$ and R are identical to those above; and m is an integer ranging from 1 to (4−(p+q+r))).

The reaction step of the present invention is, in other words, a reaction step in which there is conducted a substitution reaction of the starting alkoxysilane having an ethoxy group or a methoxy group, with an alcohol, the reaction step being characterized in that a solid acid catalyst is used therein. The reaction step of the present invention can therefore be expressed by the reaction formula below.

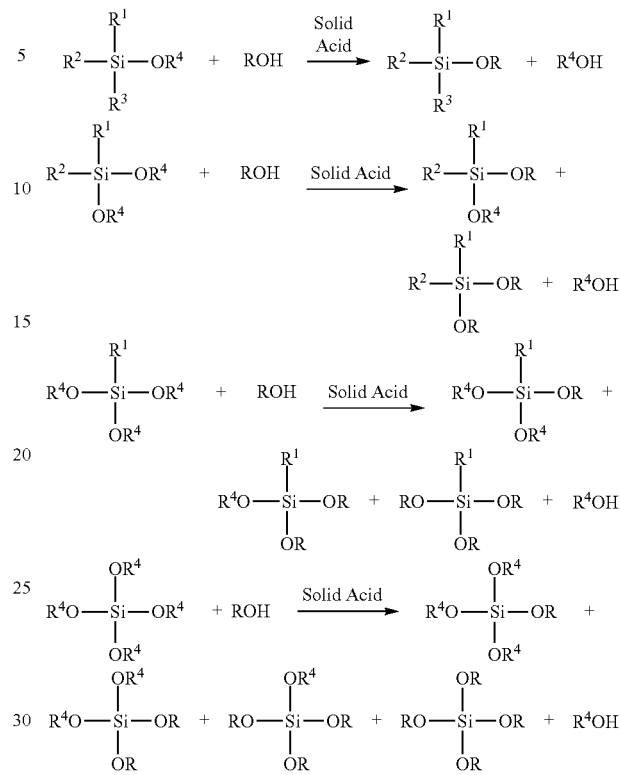

Specifically, the starting alkoxysilane having an ethoxy group or a methoxy group may be any one of monoalkoxysilane, a dialkoxysilane, a trialkoxysilane and a tetraalkoxysilane. The alkoxysilane obtained in the reaction step is not limited to being of one type, and for instance may be an alkoxysilane substituted with one alkoxy group, or an alkoxysilane substituted with two alkoxy groups, or a mixture of the foregoing, in a case where a dialkoxysilane is used as the starting material. Further, the alkoxysilane may be an alkoxysilane substituted with one alkoxy group, an alkoxysilane substituted with two alkoxy groups, an alkoxysilane substituted with three alkoxy groups, or mixtures of the foregoing, in a case where a trialkoxysilane is used as the starting material, or may be an alkoxysilane substituted with one alkoxy group, an alkoxysilane substituted with two alkoxy groups, an alkoxysilane substituted with three alkoxy groups, an alkoxysilane substituted with four alkoxy groups, or mixtures of the foregoing, in a case where a tetraalkoxysilane is used as the starting material.

Various types of conventionally known solid acid catalysts can be used in the present invention.

Specific examples of the foregoing include, for instance, solid inorganic substances such as metal salts and metal oxides. More specific instances include, zeolites, mesoporous silica, montmorillonites or the like having protic hydrogen atoms or metal cations (of aluminum, titanium, gallium, iron, cerium, scandium or the like), as well as silica gel, heteropoly acids, and inorganic solid acids having a carbon-based material as a carrier.

Among the foregoing there are preferably used zeolite-based, mesoporous silica-based or montmorillonite-based solid acids, being inorganic solid acids having a regular-pore and/or layered structure, and more preferably zeolite-based or montmorillonite-based solid acids, in terms of, for instance, catalytic activity and selectivity of products. The types of regular-pore and/or layered structure of the inorganic solid acid are not particularly limited, but the range of pore diameter of the solid acid catalyst having a porous structure is prescribed to lie in the range of 0.2 to 20 nm, preferably 0.3 to 15 nm and more preferably 0.3 to 10 nm, from the viewpoint of facilitating diffusion of reacting molecules and generated molecules. The interlayer distance in a solid acid catalyst having a layered structure is prescribed to lie in the range 0.2 to 20 nm, preferably 0.3 to 15 nm and more preferably 0.3 to 10 nm.

In a case where a zeolite is used as the inorganic solid acid catalyst having a regular-pore structure, the types thereof include various zeolites having for instance a Y-type, a beta-type, a ZSM-5-type, mordenite-type or SAPO-type basic skeleton. Zeolites can also be preferably used that are known as USY-type (Ultrastable Y-type) zeolites, for instance SUSY-type (Super Ultrastable Y), VUSY-type (Very Ultrastable Y) and SDUSY-type (Super dealuminated ultrastable Y) zeolites, obtained through secondary treatment of Y-type zeolites (Na—Y) (regarding USY-types, refer for instance to "Molecular Sieves", Advances in Chemistry, Volume 121, American Chemical Society, 1973, Chapter 19).

Preferred among the foregoing are USY-type, beta-type and Y-type zeolites, more preferably USY-type and beta-type zeolites, in terms of reaction rate. Preferably, USY-type or Y-type, and more preferably USY-type zeolites, are used as zeolites for selectively converting some groups of a plurality of ethoxy groups or methoxy groups to other alkoxy groups, from the viewpoint of a reaction rate and selectivity.

Various types of zeolite, for instance of Bronsted acid type having protic hydrogen atoms, or of Lewis acid-type having metal cations, can be used as the foregoing zeolites. Among the foregoing, protonated zeolites having protic hydrogen atoms are typified by, for instance, H—Y-type, H—SDUSY-type, H-SUSY-type, H-beta-type, H-mordenite-type, H-ZSM-5-type zeolites and the like. A zeolite can be used that results from converting an ammonium-type zeolite, for instance a $NH_4$—Y-type, $NH_4$—VUSY-type, $NH_4$-beta-type, $NH_4$-mordenite-type, or $NH_4$—ZSM-5-type zeolite, to a protonated zeolite, through firing.

Various ratios can be selected, in accordance with reaction conditions, as the silica/alumina ratio (substance amount ratio) in the zeolite. The ratio ranges ordinarily from 5 to 1000, preferably from 5 to 600, more preferably from 5 to 300 and yet more preferably from 5 to 100.

Various zeolites that comprise commercially available products can be used as the foregoing zeolites. Specific examples of commercially available products include, for instance, CBV 760, CBV 780, CBV 720, CBV 712 and CBV 600, available from Zeolyst International, as USY-type zeolites, and HSZ-360HOA and HSZ-320HOA, available from Tosoh Corporation, as Y-type zeolites. Beta-type zeolites include, for instance, CP 811C, CP 814N, CP 7119, CP 814E, CP 7105, CP 814CN, CP 811TL, CP 814T, CP 814Q, CP 811Q, CP 811E-75, CP 811E and CP 811C-300, available from Zeolyst International, HSZ-930HOA and HSZ-940HOA, available from Tosoh Corporation, and UOP-Beta available from UOP Co. Examples of mordenite-type zeolites include, for instance, CBV 21A and CBV 90A, available from Zeolyst International and HSZ-660HOA, HSZ-620HOA and HSZ-690HOA, available from Tosoh Corporation, while examples of ZSM-5-type zeolites include, for instance, CBV 5524G, CBV 8020 and CBV 8014N available from Zeolyst International.

Besides the above inorganic solid acid, an organic solid acid having an acidic functional group can be used effectively as well in a reaction where microwave irradiation is resorted to. The organic solid acid may be a polymer having acidic functional groups. Examples of types of acidic functional group include, for instance, sulfo groups, carboxy groups, phosphoryl groups and the like. Examples of types of such polymers include, for instance, Teflon-skeleton polymers having perfluoro side chains, as well as and styrene-divinylbenzene copolymers. Specific examples of the foregoing include, for instance, sulfo-group-containing Nafion (registered trademark, available from DuPont), Dowex (registered trademark, available from The Dow Chemical Company), Amberlite (registered trademark, available from Rohm and Haas Co.), and Amberlyst (registered trademark, available from The Dow Chemical Company). More specifically, examples of the foregoing include Nafion NR50, Dowex 50WX2, Dowex 50WX4, Dowex 50WX8, Amberlite IR120, Amberlite IRP-64, Amberlyst 15, Amberlyst 36 and the like. A catalyst (for instance, Nafion SAC-13 or the like) in which an organic solid acid such as Nafion is supported on an inorganic substance such as silica can also be used herein. A plurality of combinations of inorganic solid acids and organic solid acids can also be used.

The amount of catalyst with respect to the starting materials may be established arbitrarily, but ranges ordinarily from about 0.0001 to 10, preferably from about 0.001 to 8, and more preferably from about 0.001 to 6, as a weight ratio.

The reaction of the present invention can be conducted in liquid phase or gas-phase state, depending on the reaction temperature and the reaction pressure. Examples of the form of the reaction apparatus include various types of conventionally known apparatuses, for instance, batch-type and flow-type reaction apparatuses.

The reaction temperature is ordinarily −20° C. or higher, and ranges preferably from −10 to 300° C., more preferably from −10 to 200° C. In a case where the reaction is carried out at room temperature, the room temperature range is ordinarily set to 0 to 40° C., preferably 5 to 40° C. and more preferably 10 to 35° C., in order to control the reactivity of the alcohol.

The reaction pressure ranges ordinarily from 0.1 to 100 atmospheres, preferably from 0.1 to 50 atmospheres, and more preferably from 0.1 to 10 atmospheres.

The reaction time depends on, for instance, the amount of starting materials and of catalyst, the reaction temperature, the form of the reaction apparatus and so forth, but ranges ordinarily from 0.1 to 1200 minutes, preferably from 0.1 to 600 minutes and more preferably from 0.1 to 300 minutes, with productivity and efficiency in mind.

In a case where the reaction is conducted in a liquid-phase system, the reaction can take place regardless of the presence or absence of a solvent. When using a solvent, various solvents, as well as mixtures of two or more solvents can be used herein, for instance, hydrocarbons such as decalin (decahydronaphthalene), decane or the like, halogenated hydrocarbons such as chlorobenzene, 1,2- or 1,3-dichlorobenzene, 1,2,3- or 1,2,4-trichlorobenzene or the like, and ethers such as tert-butylmethyl ether and dibutyl ether, excluding solvents that react with the starting materials. When the reaction is conducted in a gas phase, the reaction can be carried out through mixing of an inert gas such as nitrogen.

The reaction of the present invention can be conducted under irradiation of microwaves. In the reaction system, the dielectric loss factor of the starting alcohol, solid acid catalyst and so forth are comparatively large, and microwaves are absorbed with good efficiency. Accordingly, the alcohol, catalyst and so forth are activated under microwave irradiation, and the reaction can be carried out more efficiently.

Various types of commercially available equipment provided with contact- or contact-less temperature sensors can be used in a microwave irradiation reaction. The microwave irradiation output, cavity type (multi-mode, single-mode), irradiation form (continuous, discontinuous) and other parameters can be established arbitrarily depending on, for instance, the scale and type of the reaction. The frequency of the microwaves ranges ordinarily from 0.3 to 30 GHz. In that range, the frequency is preferably an IMS frequency band that is allocated for use in industry, science and the medical field, and is more preferably, within that band, a 2.45 GHz band, 5.8 GHz band or the like.

A heating material (susceptor) that generates heat upon absorption of microwaves can be added to the reaction system, in order to heat up the reaction system more efficiently during the microwave irradiation reaction. Various conventionally known materials, for instance activated carbon, graphite, silicon carbide, titanium carbide or the like can be used as the type of heating material. A molded catalyst can also be used that is obtained by mixing the above-described catalyst with a powder of the heating material, and by firing and working of the mixture using an appropriate binder such as sepiolite, hormite or the like.

The reaction step of the present invention progresses in a closed-system reaction apparatus, but the reaction can be caused to progress more efficiently by using an open-system reaction apparatus, and continuously removing, out of the reaction system, ethanol or methanol that are generated as co-products in the reaction.

In the production method of the present invention there is used a solid catalyst that is insoluble in the reaction solution; as a result, it becomes possible to separate and recover the catalyst easily after the reaction step, by resorting to a method such as filtration, centrifugation or the like. The alkoxysilane that is generated can be purified easily by resorting to conventional means that are ordinarily utilized in organic chemistry, for instance, distillation, recrystallization, column chromatography and the like.

EXAMPLES

The present invention will be explained next more specifically on the basis of examples and reference examples, but the invention is not limited to these examples.

Example 1

A mixture of 1.65 mmol of methylphenyldi(methoxy)silane (Ia), 6.6 mmol of butanol (IIa) and 5 mg of CBV 780 (by Zeolyst International) was charged into a reaction tube, with stirring for 1 minute at room temperature (23° C.). The resulting product was analyzed using a gas chromatograph and a gas chromatograph/mass spectrometer. The results revealed that a mixture of butoxysilane (IIIa) (IIIa-1: methylphenyl(methoxy)(butoxy)silane and IIIa-2: methylphenyldi(butoxy)silane, IIIa-1:IIIa-2=90:10) had been generated with a yield of 88.5% (see Table 1).

Examples 2 to 98

Reactions and analyses were carried out in the same way as in Example 1, but modifying reaction conditions (starting materials, catalysts, temperature, time and so forth). The results of measurements of product yields are given in Table 1.

TABLE 1

| Example | I[1] (mmol) | II[2] (mmol) | Catalyst[3] (mg) | Silica/Alumina ratio | Heating method[4] | TEMP. (° C.) | Time (min) | III[5] | Yield[6] (%) |
|---|---|---|---|---|---|---|---|---|---|
| Example 1 | Ia (1.65) | IIa (6.7) | CBV780 (5) | 80.9 | — | 23 | 1 | IIIa (90:10) | 88.5 |
| Example 2 | Ia (1.66) | IIa (6.6) | CP814N (5) | 17.3 | — | 23 | 1 | IIIa (87:13) | 57.5 |
| Example 3 | Ia (1.65) | IIa (6.7) | CBV720 (5) | 28.5 | — | 23 | 1 | IIIa (93:7) | 84.8 |
| Example 4 | Ia (1.65) | IIa (6.7) | CBV760 (5) | 54.8 | — | 23 | 1 | IIIa (92:8) | 87.9 |
| Example 5 | Ia (1.65) | IIa (6.6) | Mont-Ti$^{3+}$ (5) | — | — | 23 | 1 | IIIa (79:21) | 51.8 |
| Example 6 | Ia (1.63) | IIa (6.8) | NR50 (5) | — | MW | 110 | 5 | IIIa (50:50) | 49.7 |
| Example 7 | Ia (1.66) | IIa (6.6) | SAC-13 (5) | — | MW | 110 | 5 | IIIa (54:46) | 84.1 |
| Example 8 | Ia (1.65) | IIa (6.7) | Dowex50Wx2 (5) | — | MW | 110 | 5 | IIIa (48:52) | 89.7 |
| Example 9 | Ia (1.66) | IIa (6.6) | CP814N (5) | 17.3 | MW | 110 | 5 | IIIa (48:52) | 89.5 |
| Example 10 | Ia (1.65) | IIa (6.7) | CP811C (5) | 39.7 | MW | 110 | 5 | IIIa (48:52) | 90.3 |
| Example 11 | Ia (1.65) | IIa (6.7) | CP811E-75 (5) | 75 | MW | 110 | 5 | IIIa (45:55) | 90.6 |
| Example 12 | Ia (1.66) | IIa (6.6) | CP811C-300 (5) | 243 | MW | 110 | 5 | IIIa (62:38) | 86.0 |
| Example 13 | Ia (1.66) | IIa (6.9) | HSZ-320H0A (5) | 5.4 | MW | 110 | 5 | IIIa (97:3) | 55.5 |
| Example 14 | Ia (1.65) | IIa (6.7) | CBV720 (5) | 28.5 | MW | 110 | 5 | IIIa (42:58) | 91.5 |
| Example 15 | Ia (1.65) | IIa (6.7) | CBV760 (5) | 54.8 | MW | 110 | 5 | IIIa (44:56) | 91.2 |
| Example 16 | Ia (1.65) | IIa (6.7) | CBV780 (5) | 80.9 | MW | 110 | 5 | IIIa (45:55) | 90.7 |
| Example 17 | Ia (1.66) | IIa (6.6) | HSZ-830H0A (5) | 29 | MW | 110 | 5 | IIIa (59:41) | 87.4 |
| Example 18 | Ia (1.65) | IIa (6.6) | HSZ-620H0A (6) | 15.7 | MW | 110 | 5 | IIIa (73:27) | 76.4 |
| Example 19 | Ia (1.65) | IIa (6.6) | Mont-Ti$^{3+}$ (5) | — | MW | 110 | 5 | IIIa (43:57) | 92.1 |
| Example 20 | Ia (1.67) | IIb (6.7) | CBV780 (5) | 80.9 | — | 23 | 1 | IIIb (100:0) | 64.8 |
| Example 21 | Ia (1.67) | IIb (6.7) | Amberlyst15 (5) | — | MW | 110 | 5 | IIIb (63:37) | 85.6 |
| Example 22 | Ia (1.65) | IIb (6.7) | CP811E-75 (5) | 75 | MW | 110 | 5 | IIIb (90:10) | 73.5 |
| Example 23 | Ia (1.66) | IIb (6.7) | HSZ-320H0A (5) | 5.4 | MW | 110 | 5 | IIIb (100:0) | 59.5 |
| Example 24 | Ia (1.67) | IIb (6.7) | CBV780 (5) | 80.9 | MW | 110 | 5 | IIIb (76:24) | 85.4 |
| Example 25 | Ia (1.66) | IIc (6.6) | CBV780 (5) | 80.9 | — | 23 | 1 | IIIc (100:0) | 65.6 |
| Example 26 | Ia (1.67) | IIc (6.6) | Amberlyst15 (5) | — | MW | 110 | 5 | IIIc (43:57) | 92.4 |
| Example 27 | Ia (1.67) | IIc (6.7) | CP811E-75 (5) | 75 | MW | 110 | 5 | IIIc (67:33) | 87.8 |
| Example 28 | Ia (1.66) | IIc (6.7) | HSZ-320H0A (5) | 5.4 | MW | 110 | 5 | IIIc (99:1) | 30.2 |
| Example 29 | Ia (1.66) | IIc (6.6) | CBV780 (5) | 80.9 | MW | 110 | 5 | IIIc (79:21) | 91.1 |

TABLE 1-continued

| Example | I[1] (mmol) | II[2] (mmol) | Catalyst[3] (mg) | Silica/ Alumina ratio | Heating method[4] | TEMP. (° C.) | Time (min) | III[5] | Yield[6] (%) |
|---|---|---|---|---|---|---|---|---|---|
| Example 30 | Ia (1.66) | IId (3.3) | NR50 (5) | — | MW | 110 | 5 | IIId (75:25) | 69.9 |
| Example 31 | Ia (1.67) | IId (3.3) | Amberlyst15 (5) | — | MW | 110 | 5 | IIId (75:25) | 71.0 |
| Example 32 | Ia (1.65) | IId (6.7) | NR50 (5) | — | MW | 110 | 5 | IIId (59:41) | 84.9 |
| Example 33 | Ia (1.65) | IId (6.7) | Amberlyst15 (5) | — | MW | 110 | 5 | IIId (60:40) | 84.9 |
| Example 34 | Ia (1.67) | IIe (6.4) | CBV300 (5) | 5.1 | MW | 110 | 5 | IIIe (72:28) | 80.3 |
| Example 35 | Ia (1.67) | IIe (6.4) | CBV600 (5) | 5.5 | MW | 110 | 5 | IIIe (94:6) | 87.1 |
| Example 36 | Ia (1.66) | IIe (6.4) | CBV720 (5) | 28.5 | MW | 110 | 5 | IIIe (57:43) | 89.3 |
| Example 37 | Ia (1.67) | IIc (6.4) | CBV760 (5) | 54.8 | MW | 110 | 5 | IIIe (57:43) | 88.5 |
| Example 38 | Ia (1.66) | IIe (6.4) | CBV780 (5) | 80.9 | MW | 110 | 5 | IIIe (63:37) | 88.1 |
| Example 39 | Ia (1.66) | IIe (6.4) | CBV600 (5) | 5.5 | MW | 100 | 5 | IIIe (98:2) | 88.9 |
| Example 40 | Ia (1.66) | IIe (6.4) | CBV600 (5) | 5.5 | MW | 80 | 5 | IIIe (99:1) | 87.3 |
| Example 41 | Ia (1.66) | IIe (6.5) | Amberlyst15 (5) | — | MW | 110 | 5 | IIIe (43:57) | 93.6 |
| Example 42 | Ib (1.27) | IIe (4.9) | Amberlyst15 (5) | — | MW | 110 | 5 | IIIf (44:37:19) | 87.1 |
| Example 43 | Ib (1.25) | IIe (4.5) | CBV780 (5) | 80.9 | MW | 110 | 5 | IIIf (96:4:0) | 81.5 |
| Example 44 | Ic (1.63) | IIe (6.5) | Amberlyst15 (5) | — | MW | 110 | 5 | IIIg (23:39:37) | 94.3 |
| Example 45 | Ic (1.65) | IIe (6.5) | CBV780 (5) | 80.9 | MW | 110 | 5 | IIIg (82:18:0) | 92.0 |
| Example 46 | Ic (1.64) | IIf (6.5) | CBV600 (5) | 5.5 | MW | 110 | 5 | IIIh (98:2:0) | 43.6 |
| Example 47 | Ic (1.67) | IIf (6.4) | CBV780 (5) | 80.9 | MW | 110 | 5 | IIIh (88:12:0) | 92.3 |
| Example 48 | Ic (1.64) | IIg (6.5) | CBV780 (5) | 80.9 | — | 23 | 1 | IIIi (99:1:0) | 36.5 |
| Example 49 | Ic (1.62) | IIg (6.5) | Amberlyst15 (5) | — | MW | 110 | 5 | IIIi (27:41:32) | 95.4 |
| Example 50 | Ic (1.62) | IIg (6.5) | CBV600 (5) | 5.5 | MW | 110 | 5 | IIIf (88:11:1) | 88.9 |
| Example 51 | Ic (1.64) | IIg (6.5) | CBV780 (5) | 80.9 | MW | 110 | 5 | IIIi (41:43:15) | 90.4 |
| Example 52 | Ic (1.64) | IIa (6.5) | Amberlyst15 (5) | — | MW | 110 | 5 | IIIj (25:38:37) | 93.3 |
| Example 53 | Ic (1.63) | IIa (6.6) | CBV780 (5) | 80.9 | — | 23 | 1 | IIIf (98:2:0) | 67.3 |
| Example 54 | Ic (1.63) | IIa (6.6) | CBV780 (5) | 80.9 | MW | 110 | 5 | IIIj (31:57:12) | 94.2 |
| Example 55 | Ic (1.66) | IIh (5.9) | CBV780 (5) | 80.9 | MW | 110 | 5 | IIIk (100:0:0) | 62.0 |
| Example 56 | Ic (1.63) | IIi (6.5) | Amberlyst15 (5) | — | MW | 140 | 5 | IIIl (44:38:18) | 84.2 |
| Example 57 | Ia (1.63) | IIa (6.8) | NR50 (6) | — | MW | 110 | 10 | IIIa (44:56) | 92.2 |
| Example 58 | Ia (1.66) | IIa (6.6) | NR50 (5) | — | OB | 110 | 10 | IIIa (51:49) | 58.6 |
| Example 59 | Ia (1.66) | IIa (6.6) | CBV600 (5) | 5.5 | — | 23 | 20 | IIIa (96:4) | 86.1 |
| Example 60 | Id (1.66) | IIa (6.6) | Amberlyst 15 (5) | — | MW | 110 | 5 | IIIm (23:38:40) | 94.0 |
| Example 61 | Id (1.66) | IIa (6.5) | CBV600 (5) | 5.5 | MW | 110 | 5 | IIIm (70:26:4) | 86.7 |
| Example 62 | Id (1.66) | IIa (6.6) | CBV780 (5) | 80.9 | MW | 110 | 5 | IIIm (29:52:19) | 94.2 |
| Example 63 | Id (1.62) | IIe (6.4) | Amberlyst 15 (5) | — | MW | 110 | 5 | IIIn (33:40:27) | 91.0 |
| Example 64 | Id (1.61) | IIe (6.4) | CBV600 (5) | 5.5 | MW | 110 | 5 | IIIp (94:6:0) | 49.3 |
| Example 65 | Id (1.63) | IIe (6.4) | CBV780 (5) | 80.9 | MW | 110 | 5 | IIIn (38:61:1) | 94.2 |
| Example 66 | Ie (1.64) | IIa (6.6) | CBV600 (5) | 5.5 | — | 23 | 1 | IIIo (63:32:6) | 77.7 |
| Example 67 | Ie (1.65) | IIa (6.6) | CBV780 (5) | 80.9 | — | 23 | 1 | IIIo (37:46:17) | 93.3 |
| Example 68 | Ie (1.65) | IIa (6.6) | Amberlyst 15 (5) | — | MW | 110 | 5 | IIIo (16:35:49) | 95.7 |
| Example 69 | Ie (1.64) | IIa (6.6) | CBV600 (5) | 5.5 | MW | 110 | 5 | IIIo (21:37:43) | 94.0 |
| Example 70 | Ie (1.65) | IIa (6.6) | CBV780 (5) | 80.9 | MW | 110 | 5 | IIIo (21:37:42) | 93.9 |
| Example 71 | Ie (1.65) | IIe (6.4) | CBV600 (5) | 5.5 | — | 23 | 1 | IIIp (74:20:5) | 46.6 |
| Example 72 | Ie (1.65) | IIe (6.4) | CBV780 (5) | 80.9 | — | 23 | 1 | IIIp (58:34:8) | 91.8 |
| Example 73 | Ie (1.63) | IIe (6.4) | Amberlyst 15 (5) | — | MW | 110 | 5 | IIIp (15:33:52) | 96.3 |
| Example 74 | Ie (1.65) | IIe (6.4) | CBV600 (5) | 5.5 | MW | 110 | 5 | IIIp (21:36:43) | 94.0 |
| Example 75 | Ie (1.65) | IIe (6.4) | CBV780 (5) | 80.9 | MW | 110 | 5 | IIIp (21:36:43) | 93.6 |
| Example 76 | If (1.60) | IIa (6.6) | Amberlyst 15 (5) | — | MW | 110 | 5 | IIIq (27:34:33:7) | 91.5 |
| Example 77 | If (1.61) | IIa (6.6) | CBV780 (5) | 80.9 | MW | 110 | 5 | IIIq (87:13:0:0) | 69.4 |
| Example 78 | If (1.61) | IIe (6.4) | Amberlyst 15 (5) | — | MW | 110 | 5 | IIIr (53:28:17:3) | 69.9 |
| Example 79 | If (1.61) | IIe (6.4) | CBV780 (5) | 80.9 | MW | 110 | 5 | IIIr (90:10:0:0) | 72.3 |
| Example 80 | Ia (1.65) | IIf (6.6) | CBV780 (5) | 80.9 | VW | 23 | 5 | IIIs (98:2) | 86.3 |
| Example 81 | Ia (1.65) | IIg (6.5) | CBV600 (5) | 5.5 | MW | 110 | 5 | IIIt (91:9) | 85.5 |
| Example 82 | Ia (1.65) | IIh (6.6) | CBV780 (5) | 80.9 | MW | 70 | 15 | IIIu (100:0) | 63.7 |
| Example 83 | Ia (1.65) | IIh (19.8) | CBV780 (5) | 80.9 | MW | 70 | 15 | IIIu (100:0) | 84.2 |
| Example 84 | Ib (1.25) | IIe (5.0) | CBV780 (5) | 80.9 | MW | 90 | 10 | IIIf (98:2:0) | 64.0 |
| Example 85 | Ib (1.25) | IIe (5.0) | CBV780 (5) | 80.9 | MW | 90 | 20 | IIIf (95:5:0) | 86.4 |
| Example 86 | Ib (1.25) | IIe (5.0) | CBV780 (5) | 80.9 | MW | 90 | 30 | IIIf (91:9:0) | 91.4 |
| Example 87 | Ib (1.25) | IIe (5.0) | CBV780 (5) | 80.9 | OB | 90 | 10 | IIIf (98:2:0) | 49.9 |
| Example 88 | Ib (1.25) | IIe (5.0) | CBV780 (5) | 80.9 | OB | 90 | 20 | IIIf (97:3:0) | 76.1 |
| Example 89 | Ib (1.25) | IIe (5.0) | CBV780 (5) | 80.9 | OB | 90 | 30 | IIIf (95:5:0) | 86.8 |
| Example 90 | Ia (1.66) | IIj (6.62) | CBV780 (5) | 80.9 | — | 23 | 1 | IIIv (79:21) | 69.1 |
| Example 91 | Ia (1.25) | IIk (15.0) | CBV780 (10) | 80.9 | MW | 50 | 30 | IIIw (100:0) | 71.9 |
| Example 92 | If (5.00) | IIe (5.5) | CBV780 (15) | 80.9 | MW | 90 | 15 | IIIc (86:14:0:0) | 70.2 |
| Example 93 | If (5.00) | IIe (5.5) | CBV720 (15) | 28.5 | MW | 90 | 15 | IIIr (89:11:0:0) | 67.7 |
| Example 94 | If (5.50) | IIl (5.0) | CBV780 (15) | 80.9 | MW | 90 | 15 | IIIx (91:9:0:0) | 65.1 |
| Example 95 | If (5.00) | IIm (5.5) | CBV780 (15) | 80.9 | MW | 90 | 15 | IIIy (91:9:0:0) | 75.1 |
| Example 96 | If (7.50) | IIn (5.0) | CBV780 (15) | 80.9 | MW | 50 | 50 | IIIz (93:7:0:0) | 62.0[7] |

TABLE 1-continued

| Example | I[1] (mmol) | II[2] (mmol) | Catalyst[3] (mg) | Silica/ Alumina ratio | Heating method[4] | TEMP. (° C.) | Time (min) | III[5] | Yield[6] (%) |
|---|---|---|---|---|---|---|---|---|---|
| Example 97 | Ia (1.65) | IIo (4.13) | CBV780 (15) | 80.9 | MW | 50 | 50 | IIIaa (99:1) | 66.0 |
| Example 98 | If (1.65) | IIo (6.60) | CBV780 (15) | 80.9 | MW | 70 | 25 | IIIab (89:11:0:0) | 64.0 |

[1] Ia: methylphenyldi(methoxy)silane, Ib: phenyltri(ethoxy)silane, Ic: phenyltri(methoxy)silane, Id: vinyltri(ethoxy)silane, Ie: tri(ethoxy)silane, If: tetra(ethoxy)silane.
[2] IIa: butanol, IIb: sec-butyl alcohol, IIc: 2-methylbutanol, IId: 2-(dimethylamino)ethanol, IIe: octanol, IIf: 3-methyl-2-butenol, IIg: benzyl alcohol, IIh: tert-butyl alcohol, IIi: 2-cyanoethanol, IIj: propargyl alcohol, IIk: tert-amyl alcohol, IIl: decanol, IIm: dodecanol, IIn: (2-hydroxyethyl)methacrylate, IIo: phenol.
[3] All zeolites used herein were zeolites after firing at 500° C. Amberlyst15: sulfo group-containing polymer Amberlyst 15 (by Dow Chemical); Dowox50Wx2: sulfo group-containing polymer Dowex 50WX2 (by Dow Chemical); CP 814N: H-beta-type zeolite CP 814N (by Zeolyst International); CP 811C: H-beta-type zeolite CP 811C (by Zeolyst International); CP 811E-75: H-beta-type zeolite CP 811E-75 (by Zeolyst International); CP 811C-300: H-beta-type zeolite CP 811C-300 (by Zeolyst International); CBV 720: H-SDUSY-type zeolite CBV 720 (by Zeolyst International); CBV 760: H-SDUSY-type zeolite CBV 760 (by Zeolyst International); CBV 780: H-SDUSY-type zeolite CBV 780 (by Zeolyst International); Tia$^{3+}$-Mont: Ti$^{3+}$-containing montmorillonite (prepared through treatment of Na$^+$-type montmorillonite in a Ti$^{3+}$ solution); NR50: sulfo group-containing polymer Nafion NR50 (by DuPont); SAC-13: sulfo group-containing polymer Nafion SAC13 (by DuPont); HSZ-320HOA: H-Y-type zeolite HSZ-320HOA (by Tosoh Corporation); CBV 720: H-SDUSY-type zeolite CBV 720 (by Zeolyst International); CBV 760: H-SDUSY-type zeolite CBV 760 (by Zeolyst International); CBV 780: H-SDUSY-type zeolite CBV 780 (by Zeolyst International); HSZ-830HOA: H-ZSM-5-type zeolite HSZ-8301HOA (by Tosoh Corporation); HSZ-620HOA: H-mordenite-type zeolite HSZ-620HOA (by Tosoh Corporation); CBV 300: NH$_4$-Y-type zeolite CBV 300 (by Zeolyst International); CBV 600: H-SUSY-type zeolite CBV 600 (by Zeolyst International).
[4] MW: Microwave reaction apparatus Initiator (by Biotage AB) (usage examples of Mw in Examples 1 to 86) or Discover (by CEM Corporation) (usage examples of Mw in Examples 90 to 96); OB: oil bath heating device MH-5D (by Rikoh Kagaku Co., Ltd.).
[5] The yields of III denote total yield of the monosubstituted product (III-1), disubstituted product (III-2), trisubstituted product (III-3) and/or tetrasubstituted product (III-4). The figures in brackets denote the respective proportions.

The various products in (IIIa) to (IIIab) were as follows.

IIIa-1: methylphenyl(methoxy)(butoxy)silane, IIIa-2: methylphenyldi(butoxy)silane;

IIIb-1: methylphenyl(methoxy)(sec-butoxy)silane, IIIb-2: methylphenyldi(sec-butoxy)silane;

IIIc-1: methylphenyl(methoxy)(2-methylbutoxy)silane, IIIc-2: methylphenyldi(2-methylbutoxy)silane;

IIId-1: methylphenyl(methoxy)[2-(dimethylamino)ethoxy]silane, IIId-2: methylphenyl bis[2-(dimethylamino)ethoxy]silane;

IIIe-1: methylphenyl(methoxy)(octoxy)silane, IIIe-2: methylphenyldi(octoxy)silane;

IIIf-1: phenyldi(ethoxy)(octoxy)silane, IIIf-2: phenyl(ethoxy)di(octoxy)silane, IIIf-3: phenyltri(octoxy)silane;

IIIg-1: phenyldi(methoxy)(octoxy)silane, IIIg-2: phenyl(methoxy)di(octoxy)silane, IIIg-3: phenyltri(octoxy)silane;

IIIh-1: phenyldi(methoxy)(3-methyl-2-butenoxy)silane, IIIh-2: phenyl(methoxy)di(3-methyl-2-butenoxy)silane;

IIIi-1: phenyldi(methoxy)(benzyloxy)silane, IIIi-2: phenyl(methoxy)di(benzyloxy)silane, IIIi-3: phenyltri(benzyloxy)silane;

IIIj-1: phenyldi(methoxy)(butoxy)silane, IIIj-2: phenyl(methoxy)di(butoxy)silane, IIIj-3: phenyltri(butoxy)silane;

IIIk-1: phenyldi(methoxy)(tert-butoxy)silane, IIIk-2: phenyl(methoxy)di(tert-butoxy)silane, IIIk-3: phenyltri(tert-butoxy)silane;

IIIl-1: phenyldi(methoxy)(2-cyanoethoxy)silane, 1111-2: phenyl(methoxy)di(2-cyanoethoxy)silane, 1111-3: phenyltri(2-cyanoethoxy)silane;

IIIm-1: vinyldi(ethoxy)(butoxy)silane, IIIm-2: vinyl(ethoxy)di(butoxy)silane, IIIm-3: vinyltri(butoxy)silane;

IIIn-1: vinyldi(ethoxy)(octoxy)silane, IIIm-2: vinyl(ethoxy)di(octoxy)silane, IIIm-3: vinyltri(octoxy)silane;

IIIo-1: di(ethoxy)(butoxy)silane, IIIo-2: (ethoxy)di(butoxy)silane, IIIo-3: tri(butoxy)silane;

IIIp-1: di(ethoxy)(octoxy)silane, IIIp-2: (ethoxy)di(octoxy)silane, IIIp-3: tri(octoxy)silane IIIq-1: tri(ethoxy)(butoxy)silane, IIIq-2: di(ethoxy)di(butoxy)silane, IIIq-3: (ethoxy)tri(butoxy)silane, IIIq-4: tetra(butoxy)silane;

IIIr-1: tri(ethoxy)(octoxy)silane, IIIr-2: di(ethoxy)di(octoxy)silane, IIIr-3: (ethoxy)tri(octoxy)silane, IIIr-4: tetra(octoxy)silane;

IIIs-1: methylphenyl(methoxy)(3-methyl-2-butenoxy)silane, IIIs-2: methylphenyldi(3-methyl-2-butenoxy)silane;

IIIt-1: methylphenyl(methoxy)(benzyloxy)silane, IIIt-2: methylphenyldi(benzyloxy)silane;

IIIu-1: methylphenyl(methoxy)(tert-butoxy)silane, IIIu-2: methylphenyldi(tert-butoxy)silane;

IIIv-1: methylphenyl(methoxy)(propargyloxy)silane, IIIy-2: methylphenyldi(propargyloxy)silane;

IIIw-1: methylphenyl(methoxy)(tert-amyloxy)silane, IIIw-2: methylphenyldi(tert-amyloxy)silane;

IIIx-1: tri(ethoxy)(decyloxy)silane, IIIx-2: di(ethoxy)di(decyloxy)silane, IIIx-3: (ethoxy)tri(decyloxy)silane, IIIx-4: tetra(decyloxy)silane;

IIIy-1: tri(ethoxy)(dodecyloxy)silane, IIIy-2: di(ethoxy)di(dodecyloxy)silane, IIIy-3: (ethoxy)tri(dodecyloxy)silane, IIIy-4: tetra(dodecyloxy)silane;

IIIz-1: tri(ethoxy)[2-(isopropenyl carbonyloxy)ethoxy]silane, IIIz-2: di(ethoxy)di[2-(isopropenyl carbonyloxy)ethoxy]silane, IIIz-3: (ethoxy)tri[2-(isopropenyl carbonyloxy)ethoxy]silane, IIIz-4: tetra[2-(isopropenyl carbonyloxy)ethoxy]silane;

IIIaa-1: methylphenyl(methoxy)(phenoxy)silane, IIIaa-2: methylphenyldi(phenoxy)silane;

IIIab-1: tri(ethoxy)(phenoxy)silane, IIIab-2: di(ethoxy)di(phenoxy)silane, IIIab-3: (ethoxy)tri(phenoxy)silane, IIIab-4: tetra(phenoxy)silane.

6) Yield with respect to I by gas chromatograph analysis.
7) Yield with respect to II by gas chromatograph analysis.

Through control of the type of catalyst and reaction conditions, the present invention allows some of the plurality of ethoxy groups or methoxy groups in the starting silane to be selectively converted to other alkoxy groups, and allows producing, as a main product, a monoalkoxysilane being a silane with m=1 in the alkoxysilane (III). When a monoalkoxysilane is the main product in the present invention, the proportion of the monoalkoxysilane in the total alkoxysilanes that are generated is ordinarily 80% or higher, preferably 85% or higher and more preferably 90% or higher.

In the examples of Table 1, where this feature is specifically exemplified, for instance, in examples 1, 3, 4, 13, 20, 22, 23, 25, 28, 35, 40, 59, 80, 81, 83, 91 and 97, where CBV 780, CBV 720, CBV 760, CBV 600, HSZ-320HOA and CP 811E-75 being USY-type, Y-type or beta-type zeolites, were used as catalysts, the ratios between compounds where one of the two methoxy groups in the starting silane was converted to an alkoxy group, and compounds where the two methoxy groups were converted, were respectively (90:10), (93:7), (92:8), (97:3), (100:0), (90:10), (100:0), (100:0), (99:1), (94:6), (99:1), (96:4), (98:2), (91:9), (100:0), (100:0) and (99:1); and compounds could be obtained, as a main product, in which just one from among the two methoxy groups was converted to another alkoxy group. In Examples 43, 46, 48, 53, 55 and 64 as well, where CBV 780 and CBV 600, being USY-type zeolites, were used as catalysts, the ratios of compounds where one from among three ethoxy groups or methoxy groups in the starting silane was converted to an alkoxy group, compounds where two of the foregoing underwent conversion, and compounds where three of the foregoing underwent conversion, were (96:4:0), (98:2:0), (99:1:0), (98:2:0), (100:0:0) and (94:6:0), respectively, and compounds could be obtained, as a main product, in which just one from among the three ethoxy groups or methoxy groups underwent conversion. In Examples 79, 94, 95 and 96, where CBV 780, being a USY-type zeolite, was used as a catalyst, the ratios between compounds where one of four ethoxy groups in the starting silane was converted to an alkoxy group, compounds where two ethoxy groups underwent conversion, compounds where three ethoxy groups underwent conversion, and compounds where four ethoxy groups underwent conversion, were (90:10:0:0), (91:9:0:0), (91:9:0:0) and (93:7:0:0), respectively, and compounds could be obtained, as a main product, in which just one from among the four ethoxy groups underwent conversion.

These results indicate that by controlling properly the reaction conditions, for instance catalyst type, temperature, time and so forth, it becomes possible to produce, as a main product, a monoalkoxysilane in which some of the ethoxy groups or methoxy groups of the starting silane are selectively converted to another alkoxy group.

As such a catalyst for selective alkoxylation there is preferably used a USY-type or Y-type zeolite catalyst, from the viewpoint of reaction rate and selectivity. However, a comparison between Example 13 and for instance Example 20 reveals that reaction rate, yield and so forth are often poorer in Y-type than in USY-type zeolites, and thus USY-type zeolites are used more preferably.

The reaction conditions such as temperature, time and so forth in selective alkoxylation are adjusted as appropriate depending on the type and amount of the starting materials and the catalyst. In a case where a zeolite catalyst is used that has comparatively high catalytic activity, the reaction temperature ranges ordinarily from 0 to 70° C., preferably from 10 to 60° C., and more preferably from about 10 to 50° C. In a case where a zeolite catalyst is used that has comparatively low catalytic activity, the reaction temperature ranges ordinarily from 50 to 150° C., preferably from 60 to 140° C. and more preferably from about 70 to 130° C. The reaction time varies depending on, for instance, the reaction temperature, but ranges ordinarily from 0.5 to 600 minutes, preferably from 0.5 to 300 minutes and more preferably from about 0.5 to 180 minutes, from the viewpoint of production efficiency.

Through a reaction between a tertiary alcohol and a methoxy or ethoxysilane, the method of the present invention, in which an inorganic solid acid is used, makes it possible to produce a silane having an alkoxy group of a tertiary alkyl group more advantageously than in a case where an organic solid acid is used as a catalyst.

For instance, in the reaction system of tert-butyl alcohol (IIh), in Examples 55 and 83 in Table 1, where a USY-type zeolite CBV 780, being a inorganic solid acid, was used as a catalyst, the substitution reaction between the methoxy group of the starting material and the alcohol proceeded smoothly, and it was possible to achieve a yield of 62.0% and 84.2%, respectively, of the target compounds IIIk and IIIu of tert-butoxysilane, having alkoxy groups of tertiary alkyl groups.

In a case where there is used a sulfo group-containing polymer, being an organic solid acid, a dehydration reaction of tert-butyl alcohol occurred, as a side reaction, and the water generated thereupon reacted with, for instance, starting methoxysilane, and, as a result a phenomenon was observed wherein the yield of the intended alkoxysilane dropped significantly. For instance, the yield of IIIk was merely 1.4% in a case where the organic solid acid Amberlyst 15 was used instead of CBV 780, as the catalyst in Example 55 above.

This reveals that the production method of the present invention, in which an inorganic solid acid is used as a catalyst, can be utilized particularly effectively in reaction systems such as those of tertiary alcohols in which dehydration reactions, as side reactions, occur readily.

In the present invention, microwave irradiation is resorted to when heating is to be performed; as a result, it becomes possible to heat more efficiently the starting materials such as the alcohol and so forth and the solid acid catalyst. In consequence, the reaction can be accelerated/promoted to a greater degree than in methods that rely on ordinary external heating using an oil bath or the like.

In an example where, for instance, phenyltri(ethoxy) silane (Ib) and octanol (IIe) were caused to react using the inorganic solid acid CBV 780 as a catalyst, the yields of octoxysilane (IIIf) for a reaction time of 10 minutes, 20 minutes and 30 minutes were 64.0%, 86.4% and 91.4%, respectively (Examples 83, 84 and 85 in Table 1), in a method in which a microwave irradiation device was used, whereas yields were 49.9%, 76.1% and 86.8%, respectively (Examples 86, 87 and 88 in Table 1) in a method in which an oil bath heating device was used. It was found thus that the method that relies on microwave irradiation affords higher yields (about 1.3-fold yield, when the reaction time is 10 minutes) than those of the method that relies on oil bath heating.

Yields and rates can be enhanced, through irradiation of microwaves, also in the case of reactions in which an organic solid acid is used as a catalyst. In an example where, for instance, methylphenyldi(methoxy)silane (Ia) and butanol (IIa) were caused to react using the organic solid acid Nafion NR50, as a catalyst, the yield of butoxysilane (IIIa), for a reaction time of 10 minutes, was 92.2% (Example 57 in Table 1), in the method in which a microwave irradiation device was used, and was 58.6% (Example 58 in Table 1) in the method in which an oil bath heating device was used. It was found thus that a method that relies on microwave irradiation affords higher yields (about 1.6-fold yield) than those of a method that relies on oil bath heating.

The above results indicate that, for identical reaction temperature and reaction time, the method of the present invention, in which microwave irradiation is resorted to, allows producing alkoxysilanes efficiently and with higher yields than in a method that involves ordinary heating by an oil bath or the like.

The reaction of the present invention may progress in a closed system or in an open system. However, the reaction can be performed efficiently, also when reducing the amount of alcohol that is used, by resorting to a method that involves actively removing, out of the reaction system, ethanol and/or methanol co-products, for instance by conducting the reaction under a stream of an inert gas such as nitrogen, in an open system, or carrying out the reaction in a depressurized system. Various instances in which the reaction is conducted under a stream of an inert gas, in an open system, will be illustrated in the following examples.

Example 99

A mixture of 3.0 mmol of methylphenyldi(methoxy)silane (Ia), 3.3 mmol of octanol (IIe) and 10 mg of CBV 600 (by Zeolyst International) was charged into a reaction tube, with stirring for 5 minutes at 110° C., using a microwave irradiation device (Discover by CEM Corporation), under a stream of nitrogen gas at a flow rate of 50 mL/minute, in an open system. The resulting product was analyzed using a gas chromatograph and a gas chromatograph/mass spectrometer. The analysis results revealed that octoxysilane (IIIe) (mixture of IIIe-1: methylphenyl(methoxy)(octoxy)silane and IIIe-2: methylphenyldi(octoxy)silane, IIIe-1: IIIe-2=97:3) was generated with a yield of 95.8%.

A reaction was conducted using identical starting materials and catalyst, with the reaction tube sealed, and the resulting product was analyzed in the same way. The analysis results revealed that the yield of (IIIe) (IIIe-1: IIIe-2=98:2) was 66.1%.

Example 100

A mixture of 1.65 mmol of methylphenyldi(methoxy) silane (Ia), 6.6 mmol of tert-butyl alcohol (IIh) and 5 mg of CBV 780 (by Zeolyst International) was charged into a reaction tube, with stirring for 15 minutes at 70° C., using a microwave irradiation device (Discover by CEM Corporation), under a stream of nitrogen gas at a flow rate of 50 mL/minute, in an open system. The resulting product was analyzed using a gas chromatograph and a gas chromatograph/mass spectrometer. The analysis result showed that methylphenyl(methoxy)(tert-butoxy)silane (IIIu-1) from tert-butoxysilane was generated with a yield of 80.3%.

A reaction was conducted using identical starting materials and catalyst, with the reaction tube sealed, and the resulting product was analyzed in the same way. The analysis results revealed that the yield of (IIIu-1) was 61.5%.

The results of Examples 99 and 100 indicate that by conducting the reaction under a stream of nitrogen gas, in an open system, the intended alkoxysilanes can be produced efficiency with higher yields than when the reactions are conducted in a closed system.

As exemplified in the following examples, the alkoxysilanes (III) obtained in the method of the present invention can be easily isolated and purified as a result of an operation that involves, for instance, separating the solid acid catalyst, by centrifugation or the like, followed by distillation.

Example 101

A mixture of 5.0 mmol of methylphenyldi(methoxy)silane (Ia), 19.9 mmol of butanol (IIa) and 15 mg of CBV 600 (by Zeolyst International) was charged into a reaction tube that was then sealed, with stirring for 20 minutes at room temperature (23° C.). The catalyst solids were separated by centrifugation, the supernatant was separated, and thereafter, the catalyst was washed with hexane (0.8 mL, twice), the supernatant and the wash solution were combined, and the resulting solution was concentrated under reduced pressure and was then distilled in a short-path distillation apparatus. As a result there were obtained 3.6 mmol (yield 71%) of methylphenyl(methoxy)(butoxy)silane (IIIa-1).

The physical property values, spectral data and so forth of (IIIa-1) were as follows.

Boiling point: 65-70° C./0.65 mmHg (distillation temperature in short-path distillation)

Element analysis: C, 63.96; H, 8.98 (measured value); C, 64.24; H, 8.98 (calculated value $C_{12}H_{20}O_2Si$);

$^1$H-NMR (CDCl$_3$): δ 0.35 (s, 3H, SiCH$_3$), 0.91 (t, J=7.3 Hz, 3H, CCH$_3$), 1.39 (sext, J=7.3 Hz, 2H, OCCCH$_2$), 1.58 (quint, J=7.3 Hz, 2H, OCCH$_2$), 3.54 (s, 3H, OCH$_3$), 3.70-3.79 (m, 2H, OCH$_2$), 7.33-7.42 (m, 3H, aromatic ring H), 7.59-7.65 (m, 2H, aromatic ring H)

$^{13}$C-NMR (CDCl$_3$): δ −4.7, 13.8, 19.0, 34.7, 50.5, 62.7, 127.8, 130.0, 134.0, 134.3

$^{29}$Si-NMR (CDCl$_3$): δ −16.2

IR (liquid film): 1592, 1465, 1430, 1387, 1258, 1190, 1121, 1087, 1039, 984, 894, 826, 802, 773, 738, 700, 652, 482, 437 cm$^{-1}$ GC-MS (EI, 70 eV): m/z (relative intensity) 209 (M$^+$-Me, 100), 153 (86), 151 (52), 146 (54), 137 (18), 123 (40), 121 (53), 105 (33), 91 (67), 77 (19), 61 (17), 59 (31), 45 (23), 43 (20), 41 (19)

Example 102

A mixture of 5.0 mmol of methylphenyldi(methoxy)silane (Ia), 19.7 mmol of sec-butyl alcohol (IIb) and 15 mg of CBV 780 (by Zeolyst International) was charged into a reaction tube that was then sealed, with stirring for 20 minutes at room temperature (23° C.). The resulting product was post-processed and distilled in the same way as in Example 101. As a result there were obtained 3.3 mmol (yield 65%) of methylphenyl(methoxy)(sec-butoxy)silane (IIIb-1).

The physical property values, spectral data and so forth of (IIIb-1) were as follows.

Boiling point: 60-70° C./0.7 mmHg (distillation temperature in short-path distillation)

Element analysis: C, 63.95; H, 8.93 (measured value); C, 64.24; H, 8.98 (calculated value $C_{12}H_{20}O_2Si$);

$^1$H-NMR (CDCl$_3$): δ 0.35 and 0.36 (each s, 3H, SiCH$_3$), 0.89 and 0.91 (each t, J=7.3 Hz, 3H, CCH$_3$), 1.19 and 1.20 (each d, each J=6.1 Hz, 3H, CHCH$_3$), 1.43-1.60 (m, 2H, CH$_2$), 3.528 and 3.535 (each s, 3H, OCH$_3$), 3.88-3.97 (m, 1H, OCH), 7.35-7.43 (m, 3H, aromatic ring H), 7.62-7.66 (m, 2H, aromatic ring H)

$^{13}$C-NMR (CDCl$_3$): δ −4.20 and −4.13, 9.99 and 10.05, 23.05 and 23.07, 32.14 and 32.17, 50.5, 70.35 and 70.37, 127.78 and 127.79, 129.9, 134.06 and 134.07, 134.85 and 134.91

$^{29}$Si-NMR (CDCl$_3$): δ −18.1

IR (liquid film): 1592, 1463, 1429, 1376, 1258, 1190, 1171, 1122, 1088, 1053, 1013, 952, 854, 822, 804, 783, 765, 738, 700, 656, 484, 460, 419 cm$^{-1}$ GC-MS (EI, 70 eV): m/z (relative intensity) 209 (M$^+$-Me, 10), 195 (30), 153 (52), 151 (91), 123 (18), 121 (46), 91 (100), 59 (21), 45 (15), 43 (15)

Example 103

A mixture of 3.3 mmol of methylphenyldi(methoxy)silane (Ia), 13.2 mmol of octanol (IIe) and 10 mg of CBV 780 (by Zeolyst International) was charged into a reaction tube that was then sealed, with stirring for 5 minutes at 110° C., using a microwave irradiation device (Initiator by Biotage AB). The resulting product was post-processed and distilled in the same way as in Example 101. As a result there were obtained 2.2 mmol (yield 68%) of methylphenyl(methoxy)(octoxy) silane (IIIe-1).

The physical property values, spectral data and so forth of (IIIe-1) were as follows.

Boiling point: 90-95° C./0.3 mmHg (distillation temperature in short-path distillation)

Element analysis: C, 68.90; H, 9.77 (measured value); C, 68.52; H, 10.06 (calculated value $C_{16}H_{28}O_2Si$);

$^1$M-NMR (CDCl$_3$): δ 0.35 (s, 3H, SiCH$_3$), 0.88 (t, J=6.9 Hz, 3H, CCH$_3$), 1.21-1.37 (m, 10H, OCC(CH$_2$)$_5$), 1.59 (quint, J=6.9 Hz, 2H, OCCH$_2$), 3.54 (s, 3H, OCH$_3$), 3.68-3.78 (m, 2H, OCH$_2$), 7.34-7.44 (m, 3H, aromatic ring H), 7.59-7.64 (m, 2H, aromatic ring H)

$^{13}$C-NMR (CDCl$_3$): δ −4.7, 14.1, 22.7, 25.8, 29.3, 29.4, 31.8, 32.5, 50.5, 63.0, 127.8, 130.0, 134.0, 134.3

$^{29}$Si-NMR (CDCl$_3$): δ −16.1

IR (liquid film): 1467, 1429, 1258, 1190, 1121, 1089, 846, 804, 775, 738, 699, 482, 434 cm$^{-1}$ GC-MS (EI, 70 eV): m/z (relative intensity) 265 (M$^+$-Me, 95), 202 (31), 187 (15), 159 (21), 153 (100), 151 (60), 145 (18), 137 (19), 123 (34), 121 (49), 105 (21), 91 (65), 69 (32), 59 (16), 55 (17), 43 (26), 41 (31)

Example 104

A mixture of 2.5 mmol of phenyltri(ethoxy)silane (Ib), 9.8 mmol of octanol (IIe) and 10 mg of CBV 780 (by Zeolyst International) was charged into a reaction tube that was then sealed, with stirring for 25 minutes at 90° C., using a microwave irradiation device (Initiator by Biotage AB). The resulting product was post-processed and distilled in the same way as in Example 101. As a result there were obtained 1.8 mmol (yield 73%) of phenyldi(ethoxy)(octoxy)silane (IIIf-1).

The physical property values, spectral data and so forth of (IIIf-1) were as follows.

Boiling point: 100-110° C./0.35 mmHg (distillation temperature in short-path distillation)

Element analysis: C, 66.62; H, 9.83 (measured value); C, 66.62; H, 9.94 (calculated value $C_{18}H_{32}O_3Si$);

$^1$H-NMR (CDCl$_3$): δ 0.88 (t, J=6.9 Hz, 3H, CCCH$_3$), 1.24 (t, J=6.9 Hz, 6H, OCCH$_3$), 1.22-1.37 (m, 10H, OCC(CH$_2$)$_5$), 1.59 (quint, J=6.9 Hz, 2H, OCCH$_2$), 3.78 (t, J=6.9 Hz, 2H, OCH$_2$CH$_3$), 3.86 (q, J=6.9 Hz, 4H, OCH$_2$CH$_3$), 7.34-7.44 (m, 3H, aromatic ring H), 7.64-7.68 (m, 2H, aromatic ring H)

$^{13}$C-NMR (CDCl$_3$): δ 14.1, 18.2, 22.7, 25.7, 29.28, 29.34, 31.8, 32.4, 58.7, 63.1, 127.8, 130.3, 131.0, 134.8

$^{29}$Si-NMR (CDCl$_3$): δ −57.7

IR (liquid film): 1457, 1431, 1390, 1167, 1129, 1100, 1083, 960, 787, 739, 700, 498 cm$^{-1}$ GC-MS (EI, 70 eV): m/z (relative intensity) 279 (M$^+$-OEt, 8), 246 (41), 203 (60), 195 (100), 189 (42), 181 (63), 167 (21), 151 (41), 149 (21), 145 (18), 139 (92), 135 (34), 134 (17), 123 (64), 121 (38), 119 (30), 110 (76), 107 (32), 105 (37), 104 (24), 91 (44), 82 (15), 81 (21), 79 (26), 77 (18), 69 (32), 68 (19), 63 (18), 55 (27), 45 (26), 43 (39), 41 (50)

Example 105

A mixture of 3.3 mmol of phenyltri(methoxy)silane (Ic), 12.9 mmol of octanol (IIe) and 10 mg of CBV 600 (by Zeolyst International) was charged into a reaction tube that was then sealed, with stirring for 15 minutes at 110° C., using a microwave irradiation device (Initiator by Biotage AB). The resulting product was post-processed and distilled in the same way as in Example 101. As a result there were obtained 2.2 mmol (yield 66%) of phenyldi(methoxy)(octoxy)silane (IIIg-1).

The physical property values, spectral data and so forth of (IIIg-1) were as follows.

Boiling point: 105-110° C./0.35 mmHg (distillation temperature in short-path distillation)

Element analysis: C, 64.77; H, 9.50 (measured value); C, 64.82; H, 9.52 (calculated value $C_{16}H_{28}O_3Si$);

$^1$H-NMR (CDCl$_3$): δ 0.87 (t, J=6.9 Hz, 3H, CCH$_3$), 1.20-1.40 (m, 10H, OCC(CH$_2$)$_5$), 1.60 (quint, J=6.9 Hz, 2H, OCCH$_2$), 3.61 (s, 6H, OCH$_3$), 3.80 (t, J=6.9 Hz, 2H, OCH$_2$), 7.34-7.46 (m, 3H, aromatic ring H), 7.63-7.68 (m, 2H, aromatic ring H)

$^{13}$C-NMR (CDCl$_3$): δ 14.1, 22.7, 25.7, 29.28, 29.32, 31.8, 32.4, 50.8, 63.2, 127.9, 129.9, 130.5, 134.7

$^{29}$Si-NMR (CDCl$_3$): δ −55.6

IR (liquid film): 1466, 1430, 1192, 1129, 1090, 819, 750, 740, 700, 483 cm$^{-1}$ GC-MS (EI, 70 eV): m/z (relative intensity) 265 (M$^+$-OMe, 0.13), 218 (17), 175 (23), 167 (100), 161 (18), 137 (24), 110 (31), 107 (32), 91 (32), 41 (20)

Example 106

A mixture of 4.8 mmol of phenyltri(methoxy)silane (Ic), 19.2 mmol of 3-methyl-2-butenol (IIf) and 10 mg of CBV 780 (by Zeolyst International) was charged into a reaction tube that was then sealed, with stirring for 5 minutes at 50° C., using a microwave irradiation device (Initiator by Biotage AB). The resulting product was post-processed and distilled in the same way as in Example 101. As a result there were obtained 3.6 mmol (yield 74%) of phenyldi(methoxy)(3-methyl-2-butenoxy)silane (IIIh-1).

The physical property values, spectral data and so forth of (IIIh-1) were as follows.

Boiling point: 90-100° C./0.8 mmHg (distillation temperature in short-path distillation)

Element analysis: C, 61.60; H, 7.93 (measured value); C, 61.87; H, 7.99 (calculated value $C_{13}H_{20}O_3Si$);

$^1$H-NMR (CDCl$_3$): δ 1.61 (s, 3H, CCH$_3$), 1.72 (d, J=1.0 Hz, 3H, CCH$_3$), 3.61 (s, 6H, OCH$_3$), 4.34 (d, J=6.9 Hz, 2H, OCH$_2$), 5.37-5.42 (m, 1H, =CH), 7.36-7.46 (m, 3H, aromatic ring H), 7.64-7.68 (m, 2H, aromatic ring H)

$^{13}$C-NMR (CDCl$_3$): δ 17.8, 25.7, 50.8, 59.9, 123.2, 127.9, 129.9, 130.5, 134.8, 135.3

$^{29}$Si-NMR (CDCl$_3$): δ −55.1

IR (liquid film): 1431, 1380, 1193, 1129, 1083, 814, 743, 701, 483 cm$^{-1}$

GC-MS (EI, 70 eV): m/z (relative intensity) 252 (M$^+$, 7.0), 237 (46), 167 (100), 159 (19), 137 (38), 131 (23), 123 (15), 107 (74), 91 (41), 77 (19), 68 (25), 67 (30), 53 (18), 41 (17)

Example 107

A mixture of 3.2 mmol of phenyltri(methoxy)silane (Ic), 13.3 mmol of benzyl alcohol (IIg) and 10 mg of CBV 600 (by Zeolyst International) was charged into a reaction tube that was then sealed, with stirring for 5 minutes at 110° C., using a microwave irradiation device (Initiator by Biotage AB). The resulting product was post-processed and distilled in the same way as in Example 101. As a result there were obtained 1.8 mmol (yield 55%) of phenyldi(methoxy)(benzyloxy)silane (IIIi-1).

The physical property values, spectral data and so forth of (IIIi-1) were as follows.

Boiling point: 100-110° C./0.5 mmHg (distillation temperature in short-path distillation)

Element analysis: C, 65.76; H, 6.55 (measured value); C, 65.66; H, 6.61 (calculated value $C_{12}H_{20}O_2Si$);

$^1$H-NMR (CDCl$_3$): δ 3.59 (s, 6H, OCH$_3$), 4.92 (s, 2H, OCH$_2$), 7.24-7.28 (m, 1H, aromatic ring H), 7.32-7.41 (m, 6H, aromatic ring H), 7.43-7.47 (m, 1H, aromatic ring H), 7.66-7.68 (m, 2H, aromatic ring H)

$^{13}$C-NMR (CDCl$_3$): δ 50.9, 64.9, 126.6, 127.3, 127.97, 127.99, 128.3, 130.7, 134.8, 140.1

$^{29}$Si-NMR (CDCl$_3$): δ −55.2

IR (liquid film): 1496, 1455, 1430, 1380, 1192, 1129, 1087, 1028, 849, 819, 757, 740, 699, 587, 490 cm$^{-1}$ GC-MS (EI, 70 eV): m/z (relative intensity) 274 (M$^+$, 6.4), 196 (70), 195 (25), 181 (43), 167 (43), 165 (16), 137 (26), 107 (27), 91 (100), 77 (21), 65 (23), 59 (24)

Example 108

A mixture of 3.2 mmol of vinyltri(ethoxy)silane (Id), 12.8 mmol of octanol (IIe) and 10 mg of CBV 600 (by Zeolyst International) was charged into a reaction tube that was then sealed, with stirring for 20 minutes at 110° C., using a microwave irradiation device (Initiator by Biotage AB). The resulting product was post-processed and distilled in the same way as in Example 101. As a result there were obtained 1.8 mmol (yield 55%) of vinyldi(ethoxy)(octoxy)silane (IIIn-1).

The physical property values, spectral data and so forth of (IIIn-1) were as follows.

Boiling point: 65-75° C./0.3 mmHg (distillation temperature in short-path distillation)

Element analysis: C, 61.17; H, 11.03 (measured value); C, 61.26; H, 11.02 (calculated value $C_{14}H_{30}O_3Si$);

$^1$H-NMR (CDCl$_3$): δ 0.88 (t, J=6.9 Hz, 3H, CCCH$_3$), 1.23 (t, J=6.9 Hz, 6H, OCCH$_3$), 1.22-1.38 (m, 10H, OCC(CH$_2$)$_5$), 1.57 (quint, J=6.9 Hz, 2H, OCCH$_2$), 3.75 (t, J=6.9 Hz, 2H, OCH$_2$CH$_2$), 3.83 (q, J=6.9 Hz, 4H, OCH$_2$CH$_3$), 5.89 (dd, J=20.6, 14.2 Hz, 1H, =CHSi), 6.01 (dd, 1H, J=20.6, 4.8 Hz, CH=CSi (cis H to Si)), 6.12 (dd, J=14.2, 4.8 Hz, CH=CSi (trans H to Si))

$^{13}$C-NMR (CDCl$_3$): δ 14.1, 18.2, 22.7, 25.7, 29.30, 29.36, 31.8, 32.5, 58.5, 62.9, 129.3 137.0

$^{29}$Si-NMR (CDCl$_3$): δ −57.7 IR (liquid film): 1467, 1390, 1168, 1101, 1083, 1010, 962, 837, 787, 763, 550 cm$^{-1}$ GC-MS (EI, 70 eV): m/z (relative intensity) 259 (M$^+$-Me, 1.9), 175 (45), 163 (27), 145 (78), 131 (100), 117 (29), 107 (17), 101 (18), 89 (32), 79 (19), 73 (15), 69 (39), 63 (28), 55 (20), 41 (18)

Example 109

A mixture of 3.2 mmol of tetra(ethoxy)silane (If), 12.7 mmol of octanol (IIe) and 10 mg of CBV 780 (by Zeolyst International) was charged into a reaction tube that was then sealed, with stirring for 7.5 minutes at 110° C., using a microwave irradiation device (Initiator by Biotage AB). The resulting product was post-processed and distilled in the same way as in Example 101. As a result there were obtained 1.6 mmol (yield 50%) of tri(ethoxy)(octoxy)silane (IIIr-1).

The physical property values, spectral data and so forth of (IIIr-1) were as follows.

Boiling point: 75-80° C./0.6 mmHg (distillation temperature in short-path distillation) Element analysis: C, 57.65; H, 10.93 (measured value); C, 57.49; H, 11.03 (calculated value $C_{14}H_{32}O_4Si$);

$^1$H-NMR (CDCl$_3$): δ 0.88 (t, J=6.9 Hz, 3H, CCCH$_3$), 1.24 (t, J=6.9 Hz, 9, OCCH$_3$), 1.22-1.37 (m, 10H, OCC(CH$_2$)$_5$), 1.58 (quint, J=6.9 Hz, 2H, OCCH$_2$), 3.76 (t, J=6.9 Hz, 2H, OCH$_2$CH$_2$), 3.85 (q, J=6.9 Hz, 6H, OCH$_2$CH$_3$)

$^{13}$C-NMR (CDCl$_3$): δ 14.1, 18.2, 22.7, 25.7, 29.30, 29.35, 31.8, 32.3, 59.1, 63.5

$^{29}$Si-NMR (CDCl$_3$): δ −81.7

IR (liquid film): 1458, 1443, 1390, 1296, 1170, 1104, 1085, 966, 841, 793, 467 cm$^{-1}$ GC-MS (EI, 70 eV): m/z (relative intensity) 292 (M$^+$, 0.35), 193 (89), 181 (77), 179 (18), 163 (21), 153 (24), 149 (100), 135 (23), 119 (20), 79 (26), 69 (43), 55 (16)

Example 110

A mixture of 5.0 mmol of methylphenyldi(methoxy)silane (Ia), 19.9 mmol of 3-methyl-2-butenol (IIe) and 15 mg of CBV 780 (by Zeolyst International) was charged into a reaction tube that was then sealed, with stirring for 1 minute at room temperature (23° C.). The resulting product was post-processed and distilled in the same way as in Example 101. As a result there were obtained 3.4 mmol (yield 68%) of methylphenyl(methoxy)(3-methyl-2-butenoxy)silane (IIIs-1).

The physical property values, spectral data and so forth of (IIIs-1) were as follows.

Boiling point: 85-95° C./0.5 mmHg (distillation temperature in short-path distillation)

$^1$H-NMR (CDCl$_3$): δ 0.36 (s, 3H, SiCH$_3$), 1.60 (s, 3H, CCH$_3$), 1.72 (d, J=1.0 Hz, 3H, CCH$_3$), 3.56 (s, 3H, OCH$_3$), 4.23-4.31 (m, 2H, OCH$_2$), 5.36-5.40 (m, 1H, =CH), 7.36-7.43 (m, 3H, aromatic ring H), 7.62-7.64 (m, 2H, aromatic ring H)

$^3$C-NMR (CDCl$_3$): δ −4.5, 17.8, 25.7, 50.5, 59.7, 123.5, 127.8, 130.0, 134.0, 134.3, 135.0

$^{29}$Si-NMR (CDCl$_3$): δ −15.4

IR (liquid film): 1679, 1592, 1447, 1430, 1380, 1259, 1191, 1121, 1083, 1065, 1029, 869, 827, 803, 773, 739, 700, 655, 481, 440 cm$^{-1}$ GC-MS (EI, 70 eV): m/z (relative intensity) 236 (M$^+$, 2.0), 221 (27), 158 (17), 153 (46), 151 (74), 143 (21), 137 (11), 131 (15), 123 (26), 121 (49), 91 (100), 67 (10), 61 (14), 59 (18), 53 (11), 45 (17), 41 (20), 39 (11)

Example 111

A mixture of 3.3 mmol of methylphenyldi(methoxy)silane (Ia), 13.3 mmol of benzyl alcohol (IIg) and 10 mg of CBV 600 (by Zeolyst International) was charged into a reaction tube that was then sealed, with stirring for 3.5 minutes at 110° C., using a microwave irradiation device (Initiator by Biotage AB). The resulting product was post-processed and distilled in the same way as in Example 101. As a result there were obtained 1.8 mmol (yield 55%) of methylphenyl (methoxy)(benzyloxy)silane (IIIt-1).

The physical property values, spectral data and so forth of (IIIt-1) were as follows.

Boiling point: 105-110° C./0.35 mmHg (distillation temperature in short-path distillation)

Element analysis: C, 69.52; H, 7.04 (measured value); C, 69.72; H, 7.02 (calculated value $C_{15}H_{18}O_2Si$);

$^1$H-NMR (CDCl$_3$): δ 0.39 (s, 3H, SiCH$_3$), 3.52 (s, 3H, OCH$_3$), 4.83 (s, 1H, OCH$^a$H$^b$), 4.86 (s, 1H, OCH$^a$H$^b$), 7.23-7.28 (m, 1H, aromatic ring H), 7.32-7.45 (m, 7H, aromatic ring H), 7.64-7.67 (m, 2H, aromatic ring H)

$^{13}$C-NMR (CDCl$_3$): δ −4.6, 50.6, 64.7, 126.6, 127.2, 127.9, 128.3, 130.2, 133.9, 134.1, 140.4

$^{29}$Si-NMR (CDCl$_3$): δ −15.0

IR (liquid film): 1592, 1496, 1454, 1429, 1379, 1259, 1208, 1190, 1121, 1086, 1028, 853, 809, 777, 738, 698, 659, 581, 482, 438 cm$^{-1}$ GC-MS (EI, 70 eV): m/z (relative intensity) 258 (M$^+$, 3.2), 225 (12), 213 (27), 211 (28), 180 (59), 165 (32), 151 (14), 121 (17), 91 (100), 65 (17), 59 (11)

Example 112

A mixture of 4.1 mmol of methylphenyldi(methoxy)silane (Ia), 48.5 mmol of tert-butyl alcohol (IIh) and 13 mg of CBV 780 (by Zeolyst International) was charged into a reaction tube that was then sealed, and stirred for 15 minutes at 70° C., using a microwave irradiation device (Discover by CEM Corporation). The resulting product was post-processed and distilled in the same way as in Example 101. As a result there were obtained 2.7 mmol (yield 65%) of methylphenyl (methoxy)(tert-butoxy)silane (IIIu-1).

The physical property values, spectral data and so forth of (IIIu-1) were as follows.

Boiling point: 70-80° C./2.8 mmHg (distillation temperature in short-path distillation)

Element analysis: C, 63.85; H, 8.86 (measured value); C, 64.24; H, 8.98 (calculated value C$_{12}$H$_{20}$O$_2$Si);

$^1$H-NMR (CDCl$_3$): δ 0.36 (s, 3H, SiCH$_3$), 1.34 (s, 9H, CCH$_3$), 3.49 (s, 3H, OCH$_3$), 7.34-7.41 (m, 3H, aromatic ring H), 7.61-7.66 (m, 2H, aromatic ring H)

$^{13}$C-NMR (CDCl$_3$): δ −1.7, 31.9, 50.3, 73.1, 127.7, 129.6, 134.0, 136.4

$^{29}$Si-NMR (CDCl$_3$): δ −23.5

IR (liquid film): 1470, 1429, 1389, 1365, 1258, 1241, 1198, 1121, 1088, 1056, 1025, 836, 808, 785, 754, 738, 714, 700, 625, 483, 442, 420, 409 cm$^{-1}$ GC-MS (EI, 70 eV): m/z (relative intensity) 209 (M$^+$-Me, 75), 153 (100), 151 (93), 123 (25), 121 (42), 91 (53), 59 (24), 45 (17), 43 (15)

Example 113

A mixture of 3.3 mmol of methylphenyldi(methoxy)silane (Ia), 13.3 mmol of butanol (IIa) and 10 mg of Amberlyst 15 (by Dow Chemical) was charged into a reaction tube, with stirring for 20 minutes at 100° C., using a microwave irradiation device (Discover by CEM Corporation), under a stream of nitrogen gas at a flow rate of 70 mL/minute, in an open system. The resulting product was post-processed and distilled in the same way as in Example 101. As a result there were obtained 2.9 mmol (yield 89%) of methylphenyldi (butoxy)silane (IIIa-2).

The physical property values, spectral data and so forth of (IIIa-2) were as follows.

Boiling point: 85-90° C./1.5 mmHg (distillation temperature in short-path distillation)

Element analysis: C, 67.70; H, 9.79 (measured value); C, 67.61; H, 9.84 (calculated value C$_{15}$H$_{26}$O$_2$Si);

$^1$H-NMR (CDCl$_3$): δ 0.34 (s, 3H, SiCH$_3$), 0.90 (t, J=7.3 Hz, 6H, CCH$_3$), 1.37 (sext, J=7.3 Hz, 4H, OCCCH$_2$), 1.56 (quint, J=7.3 Hz, 4H, OCCH$_2$), 3.69-3.77 (m, 4H, OCH$_2$), 7.38-7.42 (m, 3H, aromatic ring H), 7.60-7.65 (m, 2H, aromatic ring H)

$^{13}$C-NMR (CDCl$_3$): δ −4.3, 13.8, 19.0, 34.7, 62.6, 127.8, 129.9, 134.0, 135.0

$^{29}$Si-NMR (CDCl$_3$): δ −18.0

IR (liquid film): 1465, 1430, 1387, 1257, 1121, 1090, 1039, 984, 896, 839, 798, 774, 735, 699, 482, 435 cm$^{-1}$ GC-MS (EI, 70 eV): m/z (relative intensity) 251 (M$^+$-Me, 100), 195 (15), 193 (20), 188 (36), 139 (71), 137 (58), 121 (25), 119 (15), 91 (35), 77 (31), 45 (25), 41 (23)

Example 114

A mixture of 3.3 mmol of methylphenyldi(methoxy)silane (Ia), 8.3 mmol of octanol (IIe) and 10 mg of Amberlyst 15 (by Dow Chemical) was charged into a reaction tube, with stirring for 20 minutes at 100° C., using a microwave irradiation device (Discover by CEM Corporation), under a stream of nitrogen gas at a flow rate of 70 mL/minute, in an open system. The resulting product was post-processed and distilled in the same way as in Example 101. As a result there were obtained 2.8 mmol (yield 85%) of methylphenyldi (octoxy)silane (IIIe-2).

The physical property values, spectral data and so forth of (IIIe-2) were as follows.

Boiling point: 165-175° C./0.6 mmHg (distillation temperature in short-path distillation)

Element analysis: C, 73.32; H, 11.21 (measured value); C, 72.95; H, 11.18 (calculated value C$_{23}$H$_{42}$O$_2$Si);

$^1$H-NMR (CDCl$_3$): δ 0.34 (s, 3H, SiCH$_3$), 0.88 (t, J=7.1 Hz, 6H, CCH$_3$), 1.20-1.37 (m, 20H, OCC(CH$_2$)$_5$), 1.57 (quint, J=7.1 Hz, 4H, OCCH$_2$), 3.68-3.76 (m, 4H, OCH$_2$), 7.35-7.43 (m, 3H, aromatic ring H), 7.60-7.65 (m, 2H, aromatic ring H)

$^{13}$C-NMR (CDCl$_3$): δ −4.3, 14.1, 22.7, 25.8, 29.3, 29.4, 31.8, 32.6, 63.0, 127.8, 129.9, 134.0, 135.0

$^{29}$Si-NMR (CDCl$_3$): δ −18.0

IR (liquid film): 1467, 1429, 1257, 1121, 1093, 850, 800, 778, 736, 699, 483, 437 cm$^{-1}$ GC-MS (EI, 70 eV): m/z (relative intensity) 363 (M$^+$-Me, 100), 300 (16), 285 (28), 243 (16), 139 (56), 137 (56), 91 (23), 77 (18), 69 (56), 57 (17), 55 (26), 43 (36), 41 (36)

INDUSTRIAL APPLICABILITY

The method of the present invention allows producing, more efficiently and safely, alkoxysilanes that are useful, for instance, as various functional chemicals or synthesis intermediates thereof. The present invention is accordingly highly useful and boasts great industrial significance.

What is claimed is:

1. A method for producing alkoxysilanes, comprising a reaction step of reacting an alkoxysilane having an ethoxy group or a methoxy group, and an alcohol, in the presence of a catalyst, wherein
the alkoxysilane having an ethoxy group or methoxy group is an alkoxysilane represented by Formula (I);
the alcohol is an alcohol represented by Formula (II);
the catalyst is a solid acid catalyst; and
an alkoxysilane obtained in the reaction step is an alkoxysilane represented by Formula (III):

$$R^1_p R^2_q R^3_r Si(OR^4)_{4-(p+q+r)} \quad (I)$$

wherein in Formula (I), p, q and r are 0 or positive integers and wherein the sum of p, q and r (p+q+r) ranges from 0 to 3; R$^1$, R$^2$ and R$^3$ are each independently a hydrocarbon group having 1 to 23 carbon atoms, or a hydrogen atom; R$^4$ is independently an ethyl group or a methyl group; and in a case where R$^1$, R$^2$ and R$^3$ are hydrocarbon groups, some of the hydrogen atoms of the hydrocarbon groups may be substituted by groups that do not participate in the reaction;

wherein in Formula (II), R is a hydrocarbon group having 1 to 23 carbon atoms, and some of the hydrogen atoms in the hydrocarbon group may be substituted by groups that do not participate in the reaction;

 (III)

wherein in Formula (III), the meanings of p, q and r, and $R^1$, $R^2$, $R^3$, $R^4$ and R are identical to those above; and m is an integer ranging from 1 to (4−(p+q+r)).

2. The method for producing alkoxysilanes according to claim 1, wherein the solid acid catalyst is an inorganic solid acid having a regular-pore and/or layered structure.

3. The method for producing alkoxysilanes according to claim 2, wherein the inorganic solid acid is a zeolite and/or a montmorillonite.

4. The method for producing alkoxysilanes according to claim 3, wherein the zeolite has a silica/alumina ratio (substance amount ratio) ranging from 5 to 1000.

5. The method for producing alkoxysilanes according to claim 3, wherein the zeolite is at least one zeolite type selected from the group consisting of USY type, beta type, Y type, mordenite type and ZSM-5 type.

6. The method for producing alkoxysilanes according to claim 3, wherein an alkoxysilane, for which m in the Formula (III) is 1, is produced as a main product.

7. The method for producing alkoxysilanes according to claim 3, wherein an alkoxysilane is produced in which R in the Formula (III) is a tertiary alkyl group.

8. The method for producing alkoxysilanes according to claim 1, wherein the reaction step is performed under irradiation of microwaves.

* * * * *

UNITED STATES PATENT AND TRADEMARK OFFICE
CERTIFICATE OF CORRECTION

PATENT NO.        : 9,657,039 B2
APPLICATION NO.   : 14/772741
DATED             : May 23, 2017
INVENTOR(S)       : Hiroshi Yamashita et al.

It is certified that error appears in the above-identified patent and that said Letters Patent is hereby corrected as shown below:

On the Title Page

In Column 2 (item (56)) at Line 30, Under Other Publications, change "Cemica" to --Chemica--.

In the Specification

In Column 13-14 (TABLE 1-continued) at Line 10, Change "Me" to --IIIe--.

In Column 13-14 (TABLE 1-continued) at Line 11, Change "Me" to --IIIe--.

In Column 13-14 (TABLE 1-continued) at Line 12, Change "Me" to --IIIe--.

In Column 13-14 (TABLE 1-continued) at Line 13, Change "Me" to --IIIe--.

In Column 13-14 (TABLE 1-continued) at Line 24, Change "IIIf" to --IIIi--.

In Column 13-14 (TABLE 1-continued) at Line 27, Change "IIIf" to --IIIj--.

In Column 13-14 (TABLE 1-continued) at Line 38, Change "IIIp" to --IIIn--.

In Column 13-14 (TABLE 1-continued) at Line 66, Change "IIIc" to --IIIr--.

In Column 15 at Line 59, Change "silane" to --silane;--.

In Column 16 at Line 27, Change "IIIy-2:" to --IIIv-2:--.

In Column 20 at Line 8, Change "CCH$_2$)," to --CCH$_3$),--.

In Column 23 at Line 22, Change "(I1e)" to --(IIe)--.

Signed and Sealed this
Twenty-first Day of November, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,657,039 B2

In Column 23 at Lines 45-46, Delete "IR (liquid film): 1467, 1390, 1168, 1101, 1083, 1010, 962, 837, 787, 763, 550 cm-1" and insert the same on Column 23, Line 46, as a new paragraph.

In Column 23 at Lines 65-67, Delete "Element analysis: C 57.65, H 10.93 (measured value); C 57.49, H 11.03 (calculated value $C^{14}H^{32}O^4Si$)" and insert the same on Column 23, Line 66, as a new paragraph.

In Column 24 at Line 34, Change "$^3$C-NMR" to --$^{13}$C-NMR--.